United States Patent [19]
Hahn et al.

[11] Patent Number: 5,756,450
[45] Date of Patent: May 26, 1998

[54] WATER SOLUBLE MONOESTERS AS SOLUBILISERS FOR PHARMACOLOGICALLY ACTIVE COMPOUNDS AND PHARMACEUTICAL EXCIPIENTS AND NOVEL CYCLOSPORIN GALENIC FORMS

[75] Inventors: Lorenz Hahn, Siebnen, Switzerland; Birgit Hauer, Lahr; Ulrich Posanski, Freiburg, both of Germany

[73] Assignee: Novartis Corporation, Summit, N.J.

[21] Appl. No.: 335,523

[22] Filed: Nov. 7, 1994

Related U.S. Application Data

[63] Continuation of Ser. No. 947,224, Sep. 18, 1992, abandoned, which is a continuation of Ser. No. 791,844, Nov. 14, 1991, abandoned, which is a continuation of Ser. No. 478,187, Feb. 9, 1990, abandoned, which is a continuation-in-part of Ser. No. 243,577, Sep. 13, 1988, abandoned.

[30] Foreign Application Priority Data

| Sep. 15, 1987 | [DE] | Germany | 37 30 909.9 |
| Jan. 27, 1988 | [DE] | Germany | 38 02 355.5 |
| Feb. 9, 1989 | [GB] | United Kingdom | 8902898 |
| Feb. 9, 1989 | [GB] | United Kingdom | 8902901 |
| Feb. 13, 1989 | [GB] | United Kingdom | 8903147 |
| Feb. 17, 1989 | [GB] | United Kingdom | 8903663 |

[51] Int. Cl.$^6$ ............... A61K 38/00; A61K 38/02; C07K 5/00; C07K 7/00
[52] U.S. Cl. ............................................. 514/9; 530/317
[58] Field of Search ................................. 514/9; 530/317

[56] References Cited

U.S. PATENT DOCUMENTS

| 4,388,307 | 6/1983 | Cavanak | 424/177 |
| 4,798,823 | 1/1989 | Witzel | 514/11 |
| 4,943,560 | 7/1990 | Wigness et al. | 514/11 |

FOREIGN PATENT DOCUMENTS

| 60-7168285 | 4/1985 | Japan . | |
| 61-280435 | of 1986 | Japan | A61K 37/02 |
| 19312987 | 2/1989 | Japan . | |
| 1134878 | 11/1968 | United Kingdom | A61K 3/00 |
| 1601613 | 11/1981 | United Kingdom | A61K 9/08 |
| 2126588 | 3/1984 | United Kingdom | C07G 7/00 |

OTHER PUBLICATIONS

Chemical Abstracts No. 107: 46298;.
Chemical Abstracts No. 95: 225610 K.
Takada et al., Chem. Abstr. vol. 107 No. 6., 1986 Abst. No. 46298j.
Anon, Chem Abstr, vol. 95, 1981, p. 375, Abst. No. 225610K.
Chemical Abstracts, vol. 75, 1981, CH: 225610K.
Tatada et al. Chemical Abstract, vol. 107(1), 1986 CH: 46298J.

*Primary Examiner*—Avis M. Davenport
*Attorney, Agent, or Firm*—Hesna J. Pfeiffer; John L. Chiatalas; Carl W. Battle

[57] ABSTRACT

A combination of a pharmacologically active compound and a water soluble monoester of a saturated or unsaturated ($C_{6-18}$) fatty acid and a polyol, especially a saccharide, particularly as a solid solution of the active compound in the monoester.

The solid solution is especially suitable for substantially water insoluble active compounds, particularly such polypeptides, e.g. ciclosporins and is in all desirable weight ratios miscible with water.

The invention also, in particular, provides pharmaceutical compositions comprising a cyclosporin as active ingredient together with a fatty acid saccharide monoester.

2 Claims, 2 Drawing Sheets

WATER SOLUBLE MONOESTERS AS SOLUBILISERS FOR PHARMACOLOGICALLY ACTIVE COMPOUNDS AND PHARMACEUTICAL EXCIPIENTS AND NOVEL CYCLOSPORIN GALENIC FORMS

This is a continuation of application Ser. No. 07/947,224 filed Sep. 18, 1992 and now abandoned, which in turn is a continuation of application Ser. No. 07/791,844, filed Nov. 14, 1991 and now abandoned, which in turn is a continuation of application Ser. No. 07/478,187, filed Feb. 9, 1990 and now abandoned, which in turn is a continuation-in-part of application Ser. No. 07/243,577, filed Sep. 13, 1988 now abandoned.

The invention relates to the use of water soluble monoesters of saturated or unsaturated ($C_{6-18}$) fatty acids and polyols, preferably saccharides, as solubilisers of pharmaceutically active compounds in intravenously applicable solutions in aqueous media or in solvents which are miscible with water, e.g. polyethylene glycol, ethanol, glycerin or 1,2-propylene glycol.

[By the term "water soluble" as used herein is meant: having a solubility in water of at least 3.3% at room temperature. Water soluble monoesters as herein defined are thus monoesters dissolvable in water at room temperature in an amount of at least 1 g monoester per 30 ml water.

The term "aqueous medium" is to be understood to include systems comprising a liquid phase comprised entirely or substantially entirely of water, as well as systems in which the liquid phase additionally includes or comprises water miscible solvents such as hereinabove set forth. Preferred aqueous media are such in which the liquid phase comprises at least 75%, preferably at least 90%, most especially at least 95% water by weight.]

The invention provides a combination of such a monoester and a substantially water insoluble pharmaceutically active polypeptide, particularly a cyclopeptide, preferably a cyclosporin.

[By the term "substantially water insoluble" is meant: having a solubility in water of not more than 1% at room temperature. Substantially water insoluble polypeptides as defined above are thus polypeptides requiring at least 100 ml water to effect dissolution of 1 g thereof at room temperature. Preferably the term is applied to substances, e.g. polypeptides having a solubility in water of not more than 0.1%, in particular not more than 0.01%, e.g. not more than ca. 0.004% at room temperature.]

In a particular aspect the present invention provides pharmaceutical compositions comprising fatty acid saccharide monoesters, e.g. monoesters as aforesaid and a substantially water insoluble pharmaceutically active polypeptide, particularly a cyclopeptide, preferably a cyclosporin, as active ingredient.

The mentioned monoesters are generally known. From UK-Patent 1.134.878 it is also known, to use water soluble raffinose monoesters of the same category as solubilisers to stabilise specified non polypeptide agents, e.g. the triterpenealcoholester of 3-methoxy-4-hydroxycinnamic acid in solutions for injection or for oral application. However, and this is an important feature, considerable amounts of several other excipients (cosolubilisers) were necessary to guarantee a satisfactory stable solution (cf. page 5, lines 2–18). Hence, it follows, that for the used agent the applied monoesters alone were not satisfactory solubilisers. Additionally it appeared that the saccharose monoesters were not suitable as solubilisers at all for the used agent (cf. page 2, lines 70–73).

The products obtained are indicated for e.g. intradermal injection but not as suitable for intravenous injection (page 8, column 2, lines 3–4). Surprisingly liquid preparations according to the present invention are suitable for intravenous injection.

UK-Patent 2.126.588 relates to the stabilisation of, e.g. injectable, liquids containing tumor necrosis factor (TNF) against decomposition of the active substance employing a wide variety of non-ionic solubilisers (esters and ethers). In the examples many polyoxyethylene derivatives are discussed including inter al. sorbitan monopalmitate and sorbitan oleate. Most solubilisers are not water soluble themselves and thus not intravenously injectable. In particular the sorbitan esters are not water soluble as herein defined. Again co-solubilisers must be used (cf. page 3, lines 16–22). According to the instant invention no such excipients are neccessary.

Saccharose fatty acid esters are also mentioned in the description (not in the examples) incidentally and only the monopalmitic and the monostearic acid esters are specified (page 4, line 11). These compounds too do not meet the requirement in accordance with the instant invention, that they should be water soluble. No suggestion can be found to use water soluble monoesters for the improvement of the water solubility of pharmaceutically active polypeptides.

UK-Patent 1.601.613 discloses mixtures of non-ionic solubilisers, among others saccharose monoesters generally (page 2, line 53) and saccharose monopalmitate specifically (page 2, line 53), and agents, e.g. proteins or insulin (page 2, line 24). The indicated solubilisers (the saccharose monopalmitate is not water soluble) are used for the improvement of the resorption of agents, which are badly resorbable after oral application. There is no teaching to use the esters as solubilisers for the production of aqueous solutions, since the agents already have relatively good water solubility by nature (cf. page 1, lines 17–21 and page 2, lines 19–20). The obtained aqueous mixtures are not solutions (page 1, lines 33–39), but dispersions (page 2, line 3 and page 2, lines 63–page 3, line 4) and are recommended for rectal and not for intravenous application.

Japanese patent application no. 86 280 435 relates to the preparation of aqueous dispersions of cyclosporins for oral use. Monoesters which are applied are mostly not water soluble solubilisers, e.g. saccharose monopalmitate, saccharose monostearate or a sorbitan fatty acid ester. Saccharose monooleate was also used, but it was not found that this ester gives a clear solution.

In one of the examples a dispersion of a saccharose mono fatty acid ester and Ciclosporin is sonicated, to provide an oral liquid preparation. No indication can be found to use the obtained dispersion for intraveneous administration. For a dispersion containing 0.35% of Ciclosporin in water (3.5 mg/ml) a concentration of 0.2% monoester is employed. According to the instant invention solutions comprising 0.35% of Ciclosporin by weight are obtainable using a 2.3% solution of the water soluble saccharose monolaurate in water.

The present invention also provides compositions, in particular pharmaceutical compositions, comprising combinations of saccharose monolaurate or raffinose monolaurate with polypeptides. Such compositions may optionally include pharmaceutical excipients, which are substantially insoluble in water. Such excipients include e.g. benzene derivatives, e.g. p-hydroxybenzoic acid methyl ester.

The invention also provides solid solutions comprising pharmaceutically active, particularly substantially water insoluble pharmaceutically active compounds in the said water soluble monoesters.

Pharmaceutically active, substantially water insoluble compounds often suffer from a loss of bioavailability if applied orally. This is because they are insufficiently rapidly dissolved in the aqueous medium of the gastro-intestinal tract and are eliminated from the body, in substantial amount in undissolved form.

It is difficult to find water soluble excipients, which solubilise the pharmaceutically active compounds in aqueous media to provide solutions which are stable at all dilution stages without forming a precipitate, and which are additionally pharmaceutically acceptable. Liquid galenical forms, which are satisfactory from a pharmaceutical and medical viewpoint and which contain, in particular, substantially water insoluble polypeptides, especially cyclopeptides such as the cyclosporins, have long been sought. Excipients used in available commercial forms possess poor palatability or are associated with a risk of anaphylactic shock. Tensides containing ethylene oxide units or such having amine or amide structures are no longer acceptable from a pharmaceutical or medical viewpoint.

Surprisingly, it has now been found that in this respect unobjectionable water soluble monoesters of saturated or unsaturated ($C_{6-18}$) fatty acids and polyols, especially saccharides, are extremely well suited solubilisers, especially for pharmaceutically active, substantially water insoluble compounds. It has further been observed, that the said monoesters form solid solutions with pharmaceutically active compounds. These monoesters can dissolve the active compound sufficiently. By addition of water or other aqueous media, aqueous micellar solutions are obtained from which the active compound is readily bioavailable. The active compound is completely solubilized in the colloidal solution.

Figure 1:
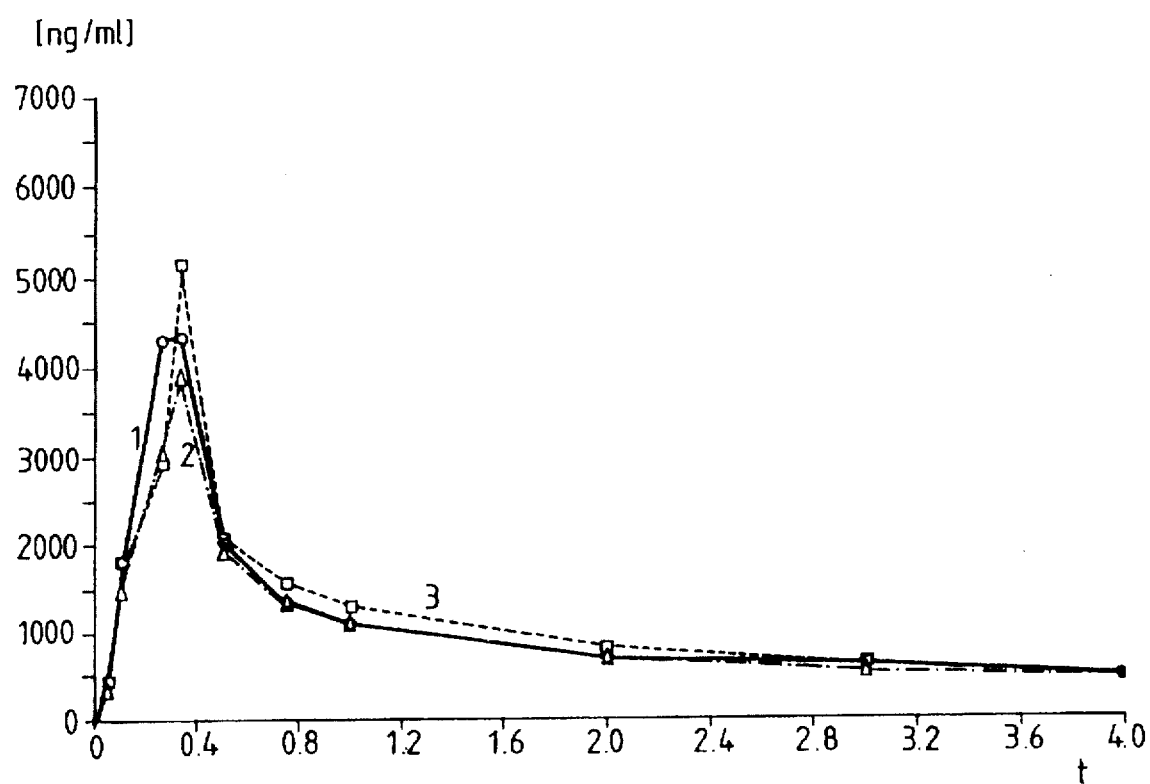
FIG. 1 is a graph illustrating that the solubilisers of this invention provide the same distribution of the Ciclosporin solutions in test animals as that of the commercial infusion concentrates.

The invention in particular provides solid solutions comprising polypeptide agents, particularly substantially water insoluble polypeptide agents in water soluble monoesters of saturated or unsaturated ($C_{6-18}$) fatty acids and polyols, especially saccharides. The fatty acid residues in the said esters may be substituted e.g. by hydroxyl.

Hydrotropic substances or cosolubilisers are not essential in the solid solutions of the invention. The used solubilisers do not contain ethylene oxide, amine or amide structural units, which are pharmaceutically or medically objectionable.

In accordance with the present invention solid solutions are obtainable in which the pharmaceutically active, e.g. substantially water insoluble, pharmaceutically active agent, e.g. polypeptide, for example a cyclosporin (i.e. the dissolved or disperse phase) is entirely or substantially entirely present in molecular distribution, or in which the water soluble fatty acid ester (i.e. the solvent or continuous phase) and the water insoluble pharmaceutically active agent are each in entirely or substantially entirely amorphous state, e.g. as verifiable by X-ray structure analysis. Solid solutions meeting the above criteria are preferred.

The water soluble fatty acid esters employed in the compositions of the invention are themselves pharmaceutically acceptable.

Preferred fatty acid esters for use in practicing the invention are monoesters of disaccharides, e.g. maltose, or, especially, saccharose, as well as of trisaccharides, e.g. raffinose. Preferred are saccharides which contain glucose, fructose and/or galactose units.

The fatty acid esters for use in practicing the invention are preferably caproic acid ($C_6$), caprylic acid ($C_8$), capric acid ($C_{10}$), lauric acid ($C_{12}$), myristic acid ($C_{14}$), palmitic acid ($C_{16}$), oleic acid ($C_{18}$), ricinoleic acid ($C_{18}$) or 12-hydroxystearic acid ($C_{18}$) esters.

In the fatty acid esters used in practicing the invention the lipophilicity of the acid moiety is, by the choice of its length, in balance with the hydrophilicity of the polyol, e.g. saccharide, moiety. Preferably ($C_{6-14}$) acid residues are connected with disaccharides and ($C_{8-18}$) acid residues with trisaccharides.

In general the HLB-value of the fatty acid ester is preferably at least 10. Suitable fatty acid esters are in particular saccharose monocaproate, saccharose monolaurate, saccharose monomyristate, saccharose monooleate and saccharose monoricinoleate, raffinose monocaproate, raffinose monolaurate, raffinose monomyristate, raffinose monopalmitate and raffinose monooleate. Saccharose monolaurate and raffinose monolaurate are especially preferred.

The monoester content of fatty acid esters used in practicing the invention is preferably at least 80%, more preferably at least 90% by weight, i.e. the said fatty acid esters preferably contain less than 20%, more preferably less than 10% of di- or poly-ester impurities. The esters can be produced in a manner known per se, e.g. as described in the Journal of the Society of Cosmetic Chemists (1956) 7 249–255 and are preferably purified by column chromatography in order to obtain a maximal monoester content.

Pharmaceutically active compounds comprised in the solid solutions of the invention are water soluble or, preferably, substantially water insoluble, e.g. Proquazone (=1-isopropyl-7-methyl-4-phenyl-2(1H)-quinazolinone) which has a water solubility of below 0.1 g/100 ml; xanthine derivatives, e.g. theophyllin; tricyclic compounds, for example tricyclic antidepressiva or e.g. ketotifen; azulene derivatives, e.g. guajazulene, or steroids, e.g. Prednisone.

Water soluble pharmaceutically active compounds are included in the invention of the solid solution, since such agents are as advantageous as substantially water insoluble agents in combination with water soluble monoesters, since their bioavailability becomes improved.

Preferred pharmaceutically active compounds in the mixtures, as well as in the solid solutions of the invention, are polypeptides, especially substantially water insoluble polypeptides having a molecular weight of from 500 to 10,000, e.g. of from 500 to 1,500.

To this class of compounds especially belong the cyclopeptides, e.g. the cyclosporins, particularly Ciclosporin, which has a water solubility of below 0.004 g/100 ml.

The present invention relates to novel galenic formulations comprising a cyclosporin as active ingredient.

The cyclosporins comprise a class of structurally distinctive, cyclic, poly-N-methylated undecapeptides, commonly possessing pharmacological, in particular immunosuppressive, anti-inflammatory and/or anti-parasitic activity. The first of the cyclosporins to be isolated was the naturally occurring fungal metabolite Ciclosporin or Cyclosporine the production and properties of which are described e.g. in U.S. Pat. No. 4,117,118., also known as cyclosporin A and commercially available under the Registered Trade Mark SANDIMMUN$^R$ or SANDIMMUNE$^R$. Ciclosporin is the cyclosporin of formula A.

```
┌─ MeBmt—αAbu—Sar—MeLeu—Val—MeLeu—Ala—(D)Ala—MeLeu—MeLeu—MeVal ─┐   (A)
│     1     2    3    4     5    6     7      8      9      10     11    │
└─────────────────────────────────────────────────────────────────────────┘
``` wherein —MeBmt— represents the N-methyl-(4R)-4-but-2E-en-1-yl-4-methyl-(L)threonyl residue of formula B

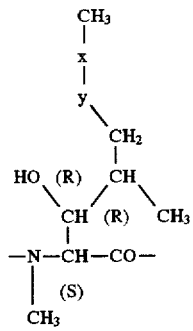 (B)

in which —x-y— is —CH=CH— (trans).

As the parent of the class Ciclosporin has so far received the most attention. The primary area of clinical investigation for Ciclosporin has been as an immunosuppressive agent, in particular in relation to its application to recipients of organ transplants, e.g. heart, lung, combined heart-lung, liver, kidney, pancreatic, bone-marrow, skin and corneal transplants and, in particular, allogenic organ transplants. In this field Ciclosporin has achieved a remarkable success and reputation.

At the same time, applicability of Ciclosporin to various autoimmune diseases and to inflammatory conditions, in particular inflammatory conditions with an aetiology including an autoimmune component such as arthritis (for example rheumatoid arthritis, arthritis chronica progrediente and arthritis deformans) and rheumatic diseases, has been intensive and reports and results in vitro, in animal models and in clinical trials are wide-spread in the literature. Specific auto-immune diseases for which Ciclosporin therapy has been proposed or applied include, autoimmune hematological disorder (including e.g. hemolytic anaemia, aplastic anaemia, pure red cell anaemia and idiopathic thrombocytopaenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine opthalmopathy, Graves disease, sarcoidosis, multiple sclerosis, primary billiary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

Further areas of investigation have been potential applicability as an anti-parasitic, in particular anti-protozoal agent, with possible uses suggested including treatment of malaria, coccidiomycosis and schistosomiasis and, yet more recently, use in cancer therapy, e.g. as an agent for reversing or abrogating resistance to other anti-neoplastic or cytostatic therapy.

Since the original discovery of ciclosporin, a wide variety of naturally occurring cyclosporins have been isolated and identified and many further non-natural cyclosporins have been prepared by total- or semi-synthetic means or by the application of modified culture techniques. The class comprised by the cyclosporins is thus now substantial and includes, for example, the naturally occurring cyclosporins A through Z [c.f. Traber et al. 1, Helv. Chim. Acta. 60, 1247–1255 (1977); Traber et al. 2, Helv. Chim. Acta. 65 no. 162, 1655–1667 (1982); Kobel et al., Europ. J. Applied Microbiology and Biotechnology 14, 273–240 (1982); and von Wartburg et al., Progress in Allergy, 38, 28–45 (1986)], as well as various non-natural cyclosporin derivatives and artificial or synthetic cyclosporins including the so called dihydro-cyclosporins [in which the moiety —x-y— of the —MeBmt— residue (Formula B above) is saturated to give —x-y—=—$CH_2$—$CH_2$—]; derivatised cyclosporins (e.g. in which a further substituent is introduced at the α-carbon atom of the sarcosyl residue at the 3-position of the cyclosporin molecule); cyclosporins in which the —MeBmt— residue is present in isomeric form (e.g. in which the configuration across positions 6' and 7' of the —MeBmt— residue is cis rather than trans); and cyclosporins wherein variant amino acids are incorporated at specific positions within the peptide sequence, employing e.g. the total synthetic method for the production of cyclosporins developed by R. Wenger—see e.g. Traber 1, Traber 2 and Kobel loc. cit.; U.S. Pat. Nos. 4,108,985, 4,210,581 and 4,220,641; European Patent Publication Nos. 0 034 567, 0 056 782 and 0 296 122; International Patent Publication No. WO 86/02080; Wenger 1, Transp. Proc. 15, Suppl. 1:2230 (1983); Wenger 2, Angew. Chem. Int. Ed., 24, 77 (1985); and Wenger 3, Progress in the Chemistry of Organic Natural Products 50, 123 (1986).

The class comprised by the cyclosporins thus now includes, for example, [Thr]$^2$-, [Val]$^2$-, [Nva]$^2$- and [Nva]$^2$-[Nva]$^5$-Ciclosporin (also known as cyclosporins C,D, G and M respectively), [3'-O-acetyl-MeBmt]$^1$-Ciclosporin (also known as cyclosporin A acetate), [Dihydro-MeBmt]$^1$-[Val]$^2$-Ciclosporin (also known as dihydro-cyclosporin D), [3'-Desoxy-3'-oxo-MeBmt]$^1$[Val]$^2$- and -[Nva]$^2$-Ciclosporin, [(D)Fluoromethyl-Sar]$^3$-Ciclosporin, [(D)Ser]$^8$-Ciclosporin, [MeIle]$^{11}$-Ciclosporin, [(D)MeVal]$^{11}$-Ciclosporin (also known as cyclosporin H), [MeAla]$^6$-Ciclosporin, [(D)Pro]$^3$-Ciclosporin and so on.

[In accordance with now conventional nomenclature for cyclosporins, these are defined by reference to the structure of Ciclosporin (i.e. Cyclosporin A). This is done by first indicating the amino acid residues present which differ from those present in Ciclosporin (e.g. "[(D)Pro]$^3$" to indicate that the cyclosporin in question has a —(D)Pro— rather than —Sar— residue at the 3-position) and then applying the term "Ciclosporin" to characterise remaining residues which are identical to those present in Ciclosporin. Individual residues are numbered starting with the residue —MeBmt—, -dihydro—MeBmt— or its equivalent in position 1.] Very many of these further cyclosporins exhibit comparable pharmaceutical utility to Ciclosporin or more specific utility, for example activity particularly in reversing tumor resistance to cytostatic therapy, and proposals for their application as therapeutic agents abound in the literature.

Dosaging for Ciclosporine (which is commercially available under the Registered Trade mark SANDIMMUN) varies considerably from subject to subject and with condition to be treated, as well as with the course of therapy and use of concommitant therapy. In general, dosaging is monitored by HPLC, RIA or equivalent assay of blood levels and individual subject dosaging is adjusted to maintain desired serum levels. Commonly, oral dosaging starts at 10 or 15–20 mg/kg day for initiating therapy, reducing to 3/5–10 mg/kg day. Intravenous infusion is at ca. 3–5 mg/kg day for initiating therapy reducing to ca. 2–3 mg/kg day for maintenance therapy (where infusion is required, e.g. in the case of rejection crisis).

Solid solutions in accordance with the present invention preferably comprise at least 7%, particularly at least 10% by weight of pharmaceutically active, substantially water insoluble pharmaceutically active, compound. The preferred upper limit for solid solutions used in an aqueous medium is the maximum weight ratio of ester to active agent soluble in the aqueous medium, that is, the maximum ratio of ester to active agent which does not precipitate out of the aqueous solution.

Solid solutions in accordance with the invention comprising a cyclosporin as active ingredient preferably comprise up to 30% of weight of cyclosporin based on the total weight of ester plus cyclosporin. Lowest concentration is only determined in relation to the therapy to be applied but should not be below 1% by weight.

Solid solutions comprising a cyclosporin in saccharose monolaurate or in raffinose monolaurate are preferred. In the first—pure—monoester solid solutions containing up to ca. 16%, in the second monoester solutions up to ca. 13.5% cyclosporin are preferred since they can be diluted with water without forming a cyclosporin precipitate. It is generally preferred to use as high a concentration as possible.

The solid solutions of the invention may be employed as, or as components of, pharmaceutical compositions. In a further aspect the present invention thus also provides: a pharmaceutical composition comprising a solid solution as herein described or defined. Such pharmaceutical compositions include dosage forms suitable for direct administration, for example unit dosage forms for oral administration, for example tablets, capsules or the like comprising or containing a solid solution in accordance with the invention. Such compositions can be prepared in accordance with conventional techniques, e.g. by appropriate forming of the solid solution or by grinding or milling of the solid solution and compounding of the obtained particulate, e.g. fine particulate, product, optionally together with other ingredients, e.g. fillers, carriers, diluents and so forth, for tabletting or for filling into capsule shells. The solid solutions of the invention may equally be employed in the manufacture of other conventional solid dosage forms, e.g. oral dosage forms such as pellets and granulates, topical dosage forms such as creams, gels, ointments and the like, e.g. for application to the skin or eye; and rectal dosage forms such as suppositories.

Oral unit dosage forms as aforesaid comprising a cyclosporin as active ingredient, for example Ciclosporin, suitably comprise from 20 to 250, preferably 25 to 100, e.g. about 50 mg cyclosporin per unit dosage.

Suitably the ratio of water soluble fatty acid ester to cyclosporin in such compositions is of the order of from 10:0.5 to 10:3.0, especially from 10:1.0 to 10:2.0, e.g. about 10:1.2 to 10:1.6 parts by weight.

Such pharmaceutical compositions also include dosage forms intended for dilution in aqueous media prior to administration, for example infusion concentrates comprising or consisting of said solid solutions, to be dissolved in an appropriate aqueous infusion medium such as physiological saline, for administration i.v., as well as preparations for dissolution in aqueous media, e.g. drink preparations and the like, prior to ingestion. To aid dissolution, such compositions will preferably comprise the solid solution in particulate, especially fine particulate, form, optionally together with other excipents or additives. Where such compositions comprise a cyclosporin as active ingredient the ratio of ester to ciclosporin will appropriately be as described above in relation to unit oral dosage forms. Compositions of this type will conveniently be presented in an appropriate container e.g. ampoule, phial, bottle or the like.

The solid solutions of the invention are readily soluble in aqueous media to provide solutions which may be further diluted to any desired concentration without clouding or precipitation. At high concentrations increase in viscosity is observed. On further dilution clear micellar solutions are formed. Such solutions are also novel and form part of the invention.

More particularly the invention provides: a solution obtained by dissolving a solid solution as herein described or defined in an aqueous medium or in a solvent which is miscible with water; as well as: a solution comprising a substantially water insoluble, pharmaceutically active polypeptide and a water soluble monoester of saturated or unsaturated ($C_{6-18}$) fatty acid and a polyol (as solubiliser for said peptide) in an aqueous medium or in a solvent which is miscible with water.

If such a liquid solution is formed by simultaneous mixing of the three components, monoester, active compound and water, a liquid solution of active compound, especially in higher concentration, is only possible after vigorous agitation. For this reason, the most simple method is, firstly preparing the solid active compound solution in the monoester, after which diluting with water can be carried out without problems. Dissolving the active compound in the liquified monoester and subsequently diluting the obtained mixture, after an optional intermediate treatment with hot ethanol, with water is known from the GB-Patent 1.134.878 (page 3, lines 22–32 and page 6, lines 34–39). However, there is no teaching that an intermediate cooling is practised and that a solid solution would have been formed.

Liquid solutions of the invention are clear or perfect or substantially clear or perfect. The pharmaceutically active component, e.g. substantially water insoluble peptide component is preferably present entirely or substantially entirely in true solution. Solutions of the invention are free or substantially free of pharmaceutically active component in colloidal or other associated or particulate form. They are free or substantially free of turbidity or clouding as may be evidenced by freedom from formation of precipitate or deposit on ultracentrifugation.

Solutions in accordance with the invention in aqueous media may of course comprise or be present together with further components other than water. They may for example also incorporate water miscible components. Such solutions equally include solutions as defined in which other non water soluble, e.g. colloidal components are present, e.g. in dispersion, for example, in the case of solutions for oral administration, flavouring agents and so forth. For the purposes of i.v. administration solutions in accordance with the invention will preferably comprise the active ingredient and the fatty acid component in an intravenously administrable aqueous medium such as isotonic saline and be free or substantially free of water insoluble additives. Liquid solutions in accordance with the invention may also be employed as or as components of occular formulations, e.g. eye drops.

The present invention accordingly also provides: a pharmaceutical composition (for example for intravenous, oral or occular administration) comprising a solution in an aqueous medium as herein described or defined.

The invention also provides using the liquid solubilisate solution as well as the solid solution orally, buccally, lingually, occularly, cutaneously, intracutaneously, percutaneously, vaginally or rectally. The solubilisate solution can additionally be applied parenterally.

Solid solutions of Ciclosporin in accordance with the present invention and aqueous solutions derived from the use are usable as alternative for the existing intravenous Ciclosporin infusion concentrate in alcohol in the presence of Cremophor$^R$ EL, a polyoxyethylated castor oil, or the oral solution in olive oil, which are the state of the art for Ciclosporin.

A comparison of Ciclosporin and saccharose or raffinose monolaurate containing aqueous solutions of the invention with the mentioned Cremophor$^R$ EL containing Ciclosporin infusion concentrate in a test in which dogs were injected intravenously with these solutions, did not show different Ciclosporin plasma concentrations. This means that the distribution of the active compound in the body is the same. In FIG. 1 the concentrations are plotted in ng/ml and the time t in hours. Curve 1 presents the saccharose monolaurate solution, curve 2 the raffinose monolaurate solution and curve 3 the commercial solution.

A comparison of a saccharose monolaurate containing Ciclosporin solution with the commercial solution in olive oil in a test in which these solutions were administered orally to rats resulted in a bio-availability improvement of 26% of the solution according to the invention.

The invention also provides a solid solution of a water soluble pharmaceutically active compound in a monoester, used according to the invention, since an improvement of bioavailability is also obtained with this type of agent.

The production of the solid solution is preferably carried out in such manner, that the agent and the sugar ester are dissolved together in a liquid solvent and the solvent is volatilised from the obtained mixture. Volatilising can be realised by evaporation or by freeze drying. As a volatile solvent water or preferably ethanol is used. If water is used, volatilising is preferably effected by freeze drying. The invention also provides a process for the production of the solid solution, comprising dissolving the active compound and the monoester together in a volatile solvent, volatilising the solvent and recovering the obtained solid solution.

The invention additionally provides a process comprising melting the monoester by heating, dissolving the active compound in the melt, solidifying by cooling and recovering the obtained solid solution. Additional pharmaceutical excipients can be added to the solid solution, e.g. to lubricate, to thicken or to dye it. Excipients which are substantially water insoluble are solubilised under the influence of the monoester and can also be incorporated in the solid solution.

Especially when the solid solution is obtained according to the firstly described process, an anti-microbiological treatment is possible before the solid solution is formed and filled in ampoules. The anti-microbiological treatment can be easily integrated in the process of production, if the solid solution is formed according to the secondly described process by raising the liquefaction temperature.

The weight ratios of the amount of active compound to the amount of monoester can be varied up to the maximum solubilisation capacity of the monoester.

The saccharose ester of lauric acid is an excipient, widely distributed in the food industry and is easily biodegradable.

The solubilisation capacity of the monoester, having a mono ester content of >80%, for Ciclosporin in aqueous solutions at room temperature and at different monoester concentrations was as follows:

TABLE I

| Saccharose monolaurate concentration in water, containing 0.9% of weight of NaCl. | Solubilising capacity for Ciclosporin in mg/ml at room temperature. |
| --- | --- |
| 1% | 1.5 mg/ml |
| 3.5 | 5.5 |
| 5 | 8.0 |
| 6.5 | 10.0 |
| 8 | 13.0 |
| 10 | 16.0 |
| 20 | 35.0 |

Figure 2:
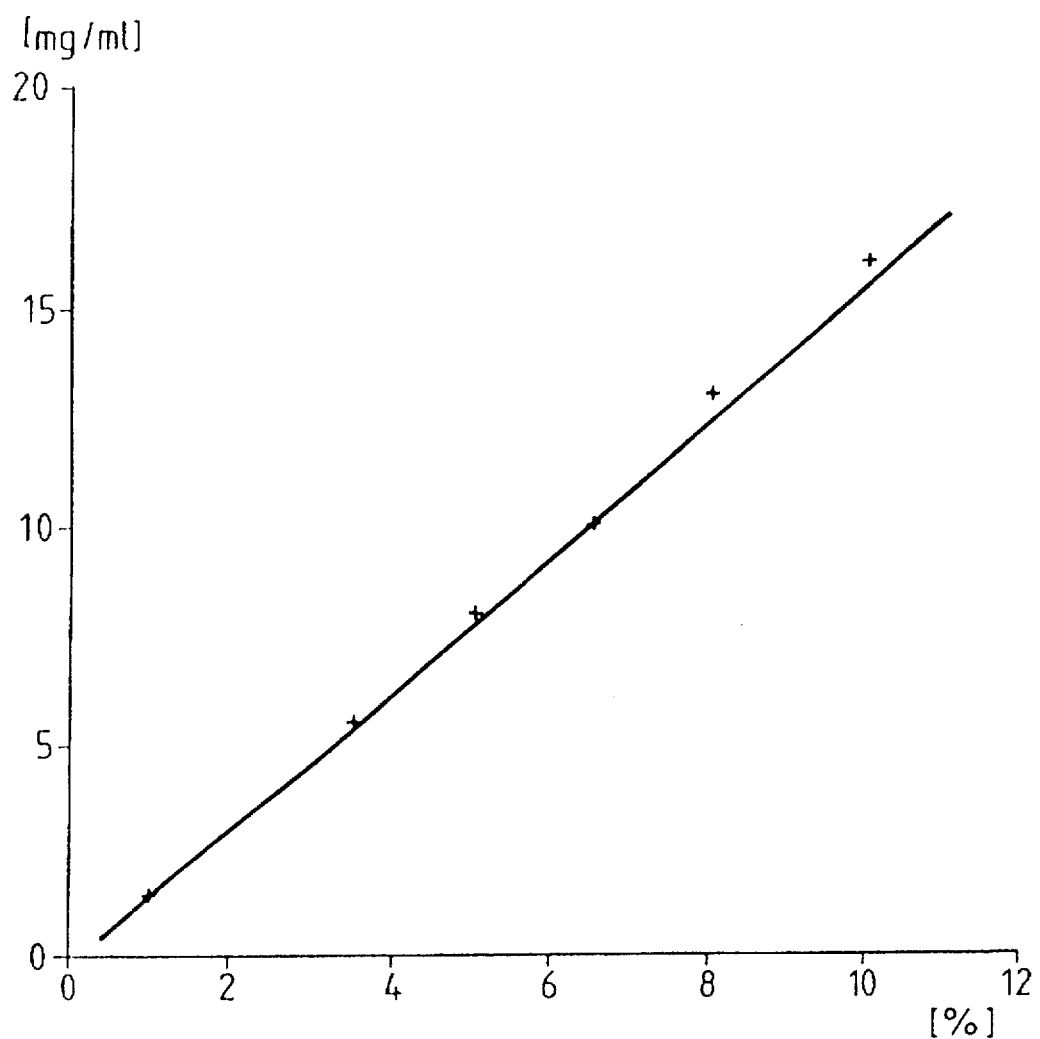
FIG. 2 is a graph of the solubilising capacity of the ciclosporin solution against the concentration of the solution, showing that a constant ration is obtained.

The solubilising capacity in mg/ml and the concentration of the solubilisator solution in % of weight are plotted in FIG. 2; a constant ratio is shown. The Ciclosporin solid solution can thus be diluted with the brine to every desirable extent, without destabilisation and precipitation of the drug compound or the solution becoming opalescent.

From table 1 it is seen that a maximum concentrated aqueous solution of Ciclosporin can be obtained if the weight ratio of the monoester to Ciclosporin is 100:16.

The present invention yet further provides a solid solution or solution in an aqueous medium as hereinbefore defined or described, for use as a pharmaceutical; as well as a method for effecting therapy employing a pharmaceutically active substance in a subject requiring treatment with said substance, which method comprises administering a solid solution or solution in an aqueous medium as herein defined or described and comprising said substance as active ingredient, in an amount sufficient to effect therapy.

As applied to the solid solutions of the invention and solutions of the invention in aqueous media comprising a cyclosporin as active ingredient the present invention accordingly provides:

a) use thereof as immunosuppressants, for the treatment of inflammatory conditions or for the treatment of parasitic disease, e.g. use in any of the diseases or conditions hereinbefore described in relation to cyclosporin, e.g. Ciclosporin, therapy, as well as b) methods of immunosuppressive, anti-inflammatory or anti-parasitic treatment, e.g. methods of treatment of any of the specific diseases or conditions hereinbefore described in relation to cyclosporin, e.g. Ciclosporin, therapy, comprising use thereof in immunosuppressive, anti-inflammatory or anti-parasitic effective amounts.

As will be apppreciated, all components of solid solutions and solutions in aqueous media for use as defined above will themselves be pharmaceutically acceptable, e.g., in relation to intravenous administration, intravenously applicable.

As hereinabove described the present invention provides, in a particular aspect, pharmaceutical compositions comprising a cyclosporin as active ingredient and a water soluble monoester of a ($C_{6-18}$) fatty acid and a saccharide [or, alternatively named, a water soluble ($C_{6-18}$) fatty acid saccharide monoester]. In accordance with the present invention compositions comprising said ingredients, as well as compositions comprising cyclosporins and fatty acid saccharide monoesters in general are of particular interest.

As previously indicated Ciclosporin has made a major contribution to the field of immunosuppressive therapy, in particular to the areas of organ transplant and the therapy of autoimmune diseases. Despite this however, difficulties encountered in providing more effective and convenient means for the administration of Ciclosporin as well as the reported occurrence of undesirable side reactions, in particular nephrotoxic reaction, have been obvious serious impediments to its wider use or application. The cyclosporins are characteristically highly hydrophobic. Proposed liquid formulations, e.g. for oral administration of cyclosporins, have hitherto been based primarily on the use of ethanol and oils or similar excipients as carrier media. Thus the commercially available Ciclosporin drink-solution employs ethanol and olive oil as carrier medium in conjunction with labrafil as a surfactant—see e.g. U.S. Pat. No. 4,388,307. Use of the drink-solution and similar compositions as proposed in the art is however accompanied by a variety of difficulties.

First, the necessity to use oils or oil based carriers may lend the preparations an unpleasant taste or otherwise reduce palatability, in particular for the purposes of long-term therapy. These effects can be masked by presentation in gelatin capsule form. However, in order to maintain the cyclosporin in solution, the ethanol content has to be kept high. Evaporation of the ethanol, e.g. from capsules or from other forms, e.g. when opened, results in the development of a cyclosporin precipitate. Where such compositions are presented in e.g. soft gelatin encapsulated form, this particular difficulty necessitates packaging of the encapsulated product in an air-tight compartment, for example an air-tight blister or aluminium-foil blister-package. This in turn renders the product both bulky and more expensive to produce. The storage characteristics of formulations as aforesaid are far from ideal.

Bioavailability levels achieved using existing oral cyclosporin dosage systems are also low and exhibit wide variation between individuals, individual patient types and even for single individuals at different times during the course of therapy. Thus reports in the literature indicate that currently available therapy employing the commercially available Ciclosporin drink solution provides an average absolute bioavailability of ca. 30% only, with marked variation between individual groups, e.g. between liver (relatively low bioavailability) and bone-marrow (relatively high bioavailability) transplant recipients. Reported variation in bioavailability between subjects has varied from anything between one or a few percent for some patients to as much as 90% or more for others. And as already noted, marked change in bioavailability for individuals with time is frequently observed.

To achieve effective immunosuppressive therapy, cyclosporin blood or blood serum levels have to be maintained within a specified range. The required range can in turn vary, depending on the particular condition being treated, e.g. whether therapy is to prevent transplant rejection or for the control of an autoimmune disease, and on whether or not alternative immunosuppressive therapy is employed concomitantly with cyclosporin therapy. Because of the wide variations in bioavailability levels achieved with conventional dosage forms, daily dosages needed to achieve required blood serum levels will also vary considerably from individual to individual and even for a single individual. For this reason it is necessary to monitor blood/blood-serum levels of patients receiving cyclosporin therapy at regular and frequent intervals. Monitoring of blood/blood-serum levels, which is generally performed by RIA or equivalent immunoassay technique, e.g. employing monoclonal antibody based technology, has to be carried out on a regular basis. This is inevitably time consuming and inconvenient and adds substantially to the overall cost of therapy.

Beyond all these very evident practical difficulties lies the occurrence of undesirable side reactions already alluded to, observed employing available oral dosage forms.

Various proposals to meet such problems have been suggested in the art, including both solid and liquid oral dosage forms. Thus Japanese patent application no. 71682/1985 to Takada et al. already referred to hereinabove, suggests the application of means for increasing the lymphatic delivery of cyclosporins, specifically by administration in conjunction with surfactants. Amongst a general listing of surfactants which may be employed are included, saccharose (sucrose) fatty acid esters, such as saccharose oleate, palmitate or stearate, as well as other fatty acid esters, in particular sorbitan fatty acid esters such as sorbitan oleate, palmitate or stearate. While use of both mono- and polyesters is indicated, a general preference for mono- or di-esters is proposed. Other surfactants listed include polyoxyethylated hydrogenated vegetable oils such as the products known and commercially available under the trade names Cremophore RH and Nikkol HCO 60, and these are clearly indicated to be preferred, e.g. to the recited saccharose ester surfactants.

Example 3 of the said Japanese application describes obtention of an aqueous preparation comprising a saccharose fatty acid ester, identified as F160, as surfactant component. The preparation comprises 3.5 mg Ciclosporin and 2 mg saccharose ester in 1 ml $H_2O$. To achieve dispersion of the Ciclosporin, sonication for 5 mins. at 100 W is required. The obtained preparation, described as "a transparent solution" is employed directly in animal models to investigate relative lymphatic resorption. Given the very low solubility of Ciclosporin in $H_2O$ and the minor amount of surfactant employed it is evident that the alleged solution is an artefact of the sonification procedure. Not only is the achieved Ciclosporin concentration inappropriately low, e.g. for an oral dosage form, the preparation is inherently unstable and hence de facto excluded as a practical, or commercial galenic form of any kind. It is essentially an experimental system enabling laboratory investigation and no more. There is no proposal to employ surfactants in any other context than in relation to lymphatic delivery.

Japanese patent application no. 193129/1987 (publication no. 038029/1989), also to Takada et al., discloses powdery preparations comprising a ciclosporin dispersed in a solid, non-surfactant, carrier phase, e.g. comprising sucrose, sorbitol, tartaric acid, urea, cellulose acetate phthalate, methacrylic acid/methyl methacrylate or hydroxypropyl methyl cellulose phthalate, together with minor amounts of a surfactant. Again the surfactant is added with the objective of increasing lymphatic delivery and, in this context, the application is clearly directed towards providing an intended practical means for applying the teachings of the aforementioned Japanese application no. 71682/1985. Reference to saccharose esters as possible surfactant components is in this case omitted. Reference to sorbitan esters amongst a listing of possible surfactant components is retained. However, products of the Nikkol HCO 60 type are again indicated to be preferred as surfactant, and Nikkol HCO 60 is the only surfactant employed in the examples. There is no indication that the alleged increase in lymphatic delivery provides any practical benefit or meets any of the difficulties in cyclosporin therapy hitherto encountered in the art, e.g. as discussed above.

By the present invention there are provided novel cyclosporin galenic formulations comprising fatty acid saccharide monoesters as primary carrier components, which meet or substantially reduce difficulties in cyclosporin, e.g Ciclosporin, therapy hitherto encountered in the art. In particular it has been found that the compositions of the invention permit the preparation of solid, semi-solid and liquid compositions containing a cyclosporin in sufficiently high concentration to permit, e.g. convenient oral administration, while at the same time achieving improved efficacy, e.g. in terms of bioavailability characteristics.

More particularly it has been found that compositions in accordance with the present invention enable effective cyclosporin dosaging with concomitant enhancement of resorption/bioavailability levels, as well as reduced variability in resorption/bioavailability levels achieved both for individual patients receiving cyclosporin therapy as well as between individuals. By application of the teachings of the present invention cyclosporin dosage forms are obtainable providing reduced variablility in achieved cyclosporin blood/blood serum levels between dosages for individual patients as well as between individuals/individual patient groups. The invention thus enables reduction of cyclosporin dosage levels required to achieve effective therapy. In addition it permits closer standardisation as well as optimisation of on-going daily dosage requirements for individual subjects receiving cyclosporin therapy as well as for groups of patients undergoing equivalent therapy.

By closer standardisation of individual patient dosaging rate and blood/blood-serum level response, as well as dosaging and response parameters for patient groups, monitoring requirements may be reduced, thus substantially reducing the cost of therapy.

By reduction of required cyclosporin dosaging/ standardisation of achieved bio-availability characteristics, the present invention also offers a means permitting reduction in the occurrence of undesirable side-effects, in particular nephrotoxic reaction, in patients undergoing cyclosporin therapy.

In addition, the present invention enables the preparation of compositions which are non-alkanol based, e.g. which may be free or substantially free of ethanol. Such compositions avoid stability and related processing difficulties as hereinbefore discussed, inherent to known alkanolic compositions. The invention thus provides inter al. compositions which are better adapted, e.g. for presentation in capsule, e.g. hard or soft gelatin capsule form and/or which eliminate or substantially reduce packaging difficulties, for example as hereinbefore discussed, e.g. for soft gelatin encapsulated forms.

Accordingly in a particular embodiment the present invention provides:

A pharmaceutical composition comprising
 (a) a cyclosporin as active ingredient and
 (b) a fatty acid saccharide monoester.

Suitably such compositions additionally comprise:
 (c) a diluent or carrier.

Component (c) may comprise any pharmaceutically acceptable diluent or carrier, whether solid, semi-solid or liquid, e.g. as known or employed in the art, including e.g. pharmaceutical grade water as hereinbefore described. Further diluents or carriers which may be employed as component (c) are described hereinafter.

Particular variants of such compositions comprising a component (c) are such as comply with any one or more of the following criteria:

i) Component (c) is a solvent with respect to both components (a) and (b), components (a) and (b) each independently having a solubility in component (c) of at least 10% at ambient temperature.

ii) Component (c) is a solvent with respect to both components (a) and (b), and components (a) and (c) are present in said composition in a ratio of 1:05 to 50 p.p.w. [(a):(c)].

iii) Component (c) is a solvent with respect to both components (a) and (b) and said composition is formulated in solid unit dosage form suitable for oral administration.

iv) Component (c) comprises a poly-($C_{2-4}$alkylene)-glycol having an average molecular weight of at most 7,000 or a viscosity at 50° C. of at most 15,000 mPa.s. or comprises a $C_{3-5}$alkylenepolyol ether or ester.

v) Said composition is, or is substantially, non aqueous.

vi) Component (c) comprises a solid polymeric carrier, an organo-silicon oxide polymer or paraffinum per- or sub-liquidum and component (a) is present in said composition in solid solution in (b).

Definitions (i) to (vi) above are to be understood as not being mutually exclusive. Compositions of the invention thus embrace compositions as defined complying with any one or more of the defined limitations (i) to (vi).

The term "pharmaceutical composition" as used herein and in the accompanying claims is to be understood as defining compositions of which the individual components or ingredients are themselves pharmaceutically acceptable, e.g. where oral administration is foreseen, acceptable for oral use or, where topical administration is foreseen, topically acceptable.

The preferred cyclosporin as component (a) is Ciclosporin. A further preferred component (a) is [Nva]$^2$-Ciclosporin, also known as cyclosporin G.

Preferred components (b) for use in the compositions of the invention are water soluble fatty acid saccharide monoesters, e.g. fatty acid monoesters of saccharides having a solubility in water of at least 3.3% at ambient temperature, i.e. which are dissolvable in water at ambient temperature in an amount of at least 1 g monoester per 30 ml water.

The fatty acid moiety of components (b) may comprise saturated or unsaturated fatty acids or mixtures thereof. Particularly suitable components (c) are $C_{6-18}$-fatty acid saccharide monoesters, in particular water soluble $C_{6-18}$-fatty acid saccharide monoesters as hereinbefore set forth. Especially suitable components (c) are caproic ($C_6$), caprylic ($C_8$), capric ($C_{10}$), lauric ($C_{12}$), myristic ($C_{14}$), palmitic ($C_{16}$), oleic ($C_{18}$), ricinoleic ($C_{18}$) and 12-hydroxystearic ($C_{18}$) acid saccharide monoesters, especially lauric acid saccharide monoesters.

The saccharide moiety of component (b) may comprise any appropriate sugar residue, e.g. mono-, di- or tri-saccharide residue. Suitably, the saccharide moiety will comprise a di- or tri-saccharide residue. Preferred components (b) comprise $C_{6-14}$-fatty acid di-saccharide monoesters and $C_{8-18}$-fatty acid tri-saccharide monoesters.

Especially suitable saccharide moieties are saccharose and raffinose residues. Particularly suitable components (b) are thus: saccharose monocaproate, saccharose monolaurate, saccharose monomyristate, saccharose monooleate, saccharose monoricinoleate, raffinose monocaproate, raffinose monolaurate, raffinose monomyristate, raffinose monopalmitate and raffinose monooleate. Most preferred components (b) are raffinose monolaurate and, especially, saccharose monolaurate.

Components (b) will suitably have a hydrophilic-lipophilic balance (HLB) of at least 10.

Components (b) suitably have an ester residue purity of at least 80%, more preferably at least 90%, most preferably at least 95%. Components (b) suitably have a melting point of from about 15° to about 60° C., more pre- ferably from about 25° to about 50° C.

By definitions (ii) and (iii) as hereinabove applied to the compositions of the invention, components (c) defined are materials in which both components (a) and (b) exhibit substantial solubility at ambient temperature, e.g. at temperatures of ca. 20° C. Preferred components (c) are materials in which (a) and (b) independently have a solubility of at least 10% [as required by definition (i)], preferably at least 25%, most preferably at least 50% (e.g. in which components (a) or (b) independently have a solubility of the order of at least 100 mg, preferably 250 mg, most preferably at least 500 mg/ml) at ambient temperature. Especially preferred are materials in which component (a) has a solubility of at least 10%, preferably at least 25%, most preferably at least 50% and/or in which component (b) has a solubility of at least 100%, more preferably at least 200%, most preferably at least 300% (e.g. in which component (b) has a solubility of the order of at least 1,000, more preferably 2,000, most preferably at least 3,000 mg/ml).

Components (c) suitable for use in the compositions of the invention include:

$c^1$) ethanol;

$c^2$) $C_{2-4}$alkylene glycols;

$c^3$) $C_{3-5}$alkylene-polyols;

$c^4$) poly-($C_{2-4}$alkylene)glycols; and $c^5$) $C_{3-5}$alkylene-polyol ethers or esters, as well as any mixture thereof. Use of ethanol, whether alone or in admixture with any other component (c), will however generally be less preferred.

When component (c) comprises a $C_{2-4}$alkylene glycol ($c^2$), this is preferably a propylene glycol, most preferably 1,2-propylene glycol. When component (c) comprises a $C_{3-5}$alkylene polyol ($c^3$), this is preferably a $C_{3-5}$alkylene triol, most preferably glycerol.

When component (c) comprises a poly-($C_{2-4}$alkylene) glycol ($c^4$), this is suitably a polyethylene glycol. For use in the compositions of the invention, such components preferably have an average molecular weight of not more than about 7,000 [cf. definition (iv)], e.g. up to 6,600, more preferably of not more than about 2,000, e.g. up to 1,600, most preferably of not more than about 500. Preferably such components have a viscosity of at most about 15,000 mPa.s., more preferably at most about 1,000 mPa.s., most preferably at most about 200 mPa.s., at 50° C. or, more suitably, at ambient temperatures [cf. definition (iv)]. Suitable polyethylene glycols for use as components (c) are, e.g. as described in Fiedler, Lexikon der Hilfstoffe, 2 nd. revised and expanded edition, [1981] Vol. 2, at pages 726 to 731, in particular the products PEG (polyethylene glycol) 200, 300, 400 and 600, as well as PEG 1000, 2000, 4000 or 6000, but especially 200, 300 and 400, e.g. conforming to the following approximate physical characteristics:

|  | PEG 200 | PEG 300 | PEG 400 | PEG 600 |
|---|---|---|---|---|
| mol. wt. | ca. 190–210 | ca. 285–215 | ca. 380–420 | ca. 570–630 |
| viscosity mPa · s. | ca. 46–53 | ca. 66–74 | ca. 85–95 | ca. 130–150 |
| freezing point | ca. –50° C. | ca. –16 to –12° C. | ca. –3 to 8° C. | ca. 15 to 25° C. |
| $n_D^{25}$ | ca. 1.459 | ca. 1.463 | ca. 1.465 | ca. 1.467 |

When component (c) comprises a $C_{3-5}$alkylene polyol ether or ester ($c^5$), this is suitably a $C_{3-5}$alkylene triol, in particular glycerol, ether or ester. Suitable components ($c^5$) include mixed ethers or esters, i.e. components including other ether or ester ingredients, for example transesterification products of $C_{3-5}$alkylene triol esters with other mono-, di- or poly-ols.

Particularly suitable components ($c^5$) are mixed $C_{3-5}$alkylene triol/poly-($C_{2-4}$alkylene) glycol fatty acid esters, especially mixed glycerol/polyethylene- or polypropylene-glycol fatty acid esters.

Especially suitable components ($c^5$) for use in accordance with the present invention include products obtainable by transesterification of glycerides, e.g. triglycerides, with poly-($C_{2-4}$alkylene) glycols, e.g. poly-ethylene glycols and, optionally, glycerol. Such transesterification products are generally obtained by alcoholysis of glycerides, e.g. triglycerides, in the presence of a poly-($C_{2-4}$alkylene) glycol, e.g. polyethylene glycol and, optionally, glycerol (i.e. to effect transesterification from the glyceride to the poly-alkylene glycol/glycerol component, i.e. via poly-alkylene glycolysis/glycerolysis). In general such reaction is effected by reaction of the indicated components (glyceride, polyalkylene glycol and, optionally, glycerol) at elevated temperature under an inert atmosphere with continuous agitation.

Preferred glycerides are fatty acid triglycerides, e.g. ($C_{10-22}$fatty acid) triglycerides, including natural and hydrogenated oils, in particular vegetable oils. Suitable vegetable oils include, for example, olive, corn, almond, peanut, coconut, palm, soybean and wheat oils and, in particular, natural or hydrogenated oils rich in ($C_{12-16}$fatty acid) ester residues.

Preferred polyalkylene glycol materials are polyethylene glycols, in particular polyethylene glycols having a molecular weight of from ca. 500 to ca. 4,000, e.g. from ca. 1,000 to ca. 2,000.

Suitable components ($c^5$) thus comprise mixtures of $C_{3-5}$alkylene triol esters, e.g. mono-, di- and trimesters in variable relative amount, and poly($C_{2-4}$alkylene) glycol mono- and di-esters, together with minor amounts of free $C_{3-5}$alkylene triol and free poly-($C_{2-5}$alkylene) glycol. As hereinabove set forth, the preferred alkylene triol moiety is glyceryl; preferred polyalkylene glycol moieties will be polyethylene glycyl, in particular having a molecular weight of from ca. 500 to ca. 4,000; and preferred fatty acid moieties will be $C_{10-22}$fatty acid ester residues, in particular saturated $C_{10-22}$fatty acid ester residues.

Particularly suitable components ($c^5$) may thus alternatively be defined as:

transesterification products of a natural or hydrogenated vegetable oil and a polyethylene glycol and, optionally, glycerol; or compositions comprising or consisting of glyceryl mono-, di- and tri-$C_{10-22}$fatty acid esters and polyethylene glycyl mono- and di-$C_{10-22}$fatty acid esters (optionally together with, e.g. minor amounts of free glycerol and free polyethylene glycol).

Preferred vegetable oils, polyethylene glycols or polyethylene glycol moieties and fatty acid moieties in relation to the above definitions are as hereinbefore set forth. Particularly suitable components ($c^5$) as described above for use in the present invention are those known and commercially available under the trade name Gelucir, in particular the products i) Gelucir 33/01, which has an m.p. = ca. 33–38° C. and a saponification no. = ca. 240/260;

ii) Gelucir 35/10, m.p. = ca. 29–34° C., saponification no. = ca. 120–140;

iii) Gelucir 37/02, m.p. = ca. 34–40° C., saponification no. = ca. 200–220;

-continued iv) Gelucir 42/12, m.p. = ca. 41–46° C., saponification no. = ca. 95–115;
v) Gelucir 44/14, m.p. = ca. 42–46° C., saponification no. = ca. 75–95;
vi) Gelucir 46/07, m.p. = ca. 47–52° C., saponification no. = ca. 125–145;
vii) Gelucir 48/09, m.p. = ca. 47–52° C., saponification no. = ca. 105–125;
viii) Gelucir 50/02, m.p. = ca. 48–52° C., saponification no. = ca. 180–200;
ix) Gelucir 50/13, m.p. = ca. 46–41° C., saponification no. = ca. 65–85;
x) Gelucir 53/10, m.p. = ca. 48–53° C., saponification no. = ca. 95–115;
xi) Gelucir 62/05, m.p. = ca. 60–65° C., saponification no. = ca. 70–90.

Products (i) to (x) above all have an acid value=<2. Product (xi) has an acid value=<5. Products (ii), (iii) and (vi) to (x) above all have an iodine no.=<3. Product (i) has an iodine no.=≦8. Products (iv) and (v) have an iodine no.=<5. Product (xi) has an iodine no.=<10. Components ($c^5$) having an iodine no.=<1 will generally be preferred. As will be appreciated, mixtures of components ($c^5$) as defined may also be employed in the compositions of the invention.

When a component (c) as hereinabove particularly described [i.e. component complying with any of the definitions (i) to (iv) hereinabove or any component as defined under ($c^1$) to ($c^5$)] is employed, the compositions of the invention will generally comprise component (a) in a carrier medium comprising components (b) and (c). Commonly components (a) and (b) will each be present in the compositions of the invention in dispersion or solution, e.g. molecular or miscellar dispersion or solution, (including, where appropriate, solid solution). Thus component (a) will generally be present in dispersion or solution in both components (b) and (c) and components (b) will in turn be present in solution in (c). Component (b) will generally act in the compositions of the invention as a carrier or solubilizor (either pre- and/or post-administration) for component (a), and component (c) will act as a carrier or fluidizer. (The present invention is, of course, not to be understood as being in anyway restricted to any particular functional relationship between the components (a), (b) and (c), unless otherwise specified.)

It is preferred that, when a component (c) as aforesaid is employed, the compositions of the invention should be formulated in solid unit dosage form suitable for oral administration, for example presented in hard or soft gelatin encapsulated form suitable for oral administration [cf. definition (iii)]. Such unit dosage forms will, as hereinafter described in greater detail, suitably comprise, e.g. from 2 to 200 mg of component (a) per unit dose.

When a component (c) as aforesaid is employed, components (a) and (c) will preferably be present in the compositions of the invention in a ratio of from 1:0.5 to 50 p.p.w. [(a):(c)] [cf. definition (ii)]. Components (a) and (b) will suitably be present in a ratio of from 1:3 to 200 p.p.w. [(a):(b)].

When a component (c) as aforesaid is employed it is yet further preferred that the compositions of the invention should be non-aqueous or substantially non-aqueous [cf. definition (v)], e.g. have a water content of less than 20%, more preferably less than 10%, yet more preferably less than 5%, 2%, or 1%, based on the total weight of the composition.

In accordance with the foregoing, the present invention also provides, in a series of particular embodiments:

A pharmaceutical composition comprising a component (a) and a component (b) as hereinbefore defined and a diluent selected from any one of components ($c^1$) to ($c^4$) as hereinbefore defined, or any mixture thereof, and complying with anyone of definitions (ii) to (v) hereinabove;

A pharmaceutical composition comprising a component (a), (b) and ($c^2$) as hereinbefore defined and complying with definitions (ii), (iii) or (v) hereinabove; and A pharmaceutical composition comprising a component (a), (b) and ($c^5$) as hereinbefore defined.

When a component (c) as hereinbefore particularly described [i.e. component complying with anyone of the definitions (i) to (iv) or any of components ($c^1$) to ($c^5$)] is employed in the said compositions of the invention, components (a) and (c) are suitably present in said compositions in a ratio of about 1:0.5 to 50 p.p.w. More suitably components (a) and (c) are present in a ratio of about 1:1 to 10, more preferably 1:1 to 5, most preferably about 1:1.5 to 2.5, e.g. about 1:1.6 or 1:2 p.p.w. [(a):(c)]. Components (a) and (b) are suitably present in the said compositions in a ratio of about 1:3 to 200, preferably about 1:3 to 100, more preferably about 1:3 to 50 p.p.w. (e.g. in a ratio of about 1:3.33 to 20 p.p.w. More suitably components (a) and (b) are present in a ratio of about 1:5 to 20, preferably about 1:5 to 10 (e.g. about 1:6.25 to 8.33), most preferably about 1:6.0 to 6.5, e.g. about 1:6.25 p.p.w. [(a):(b)].

When the compositions of the invention comprise saccharose monolaurate as component (b) and 1,2-propylene glycol as component (c), components (a) and (b) are preferably present in a ratio of from about 1:6 to 7 p.p.w. [(a):(b)] and components (a) and (c) are preferably present in a ratio of from about 1:1.5 to 2.5, e.g. about 1:2 p.p.w. [(a):(c)].

Compositions in accordance with the present invention comprising a component (c) as aforesaid may be made up in any appropriate dosage form, e.g. for oral, parenteral or topical application, for example for dermal or ophthalmic application, e.g. for application to the surface of the eye, e.g. for the treatment of autoimmune conditions of the eye such as hereinbefore set forth, or for intralesional injection, e.g. in the treatment of psoriasis.

Suitably such compositions will be made up in unit dosage form, whether for oral administration or otherwise.

The amount of component (a) present in such unit dosage forms will of course vary depending on e.g. the condition to be treated, the intended mode of administration and the effect desired. In general however, such unit dosage forms will suitably comprise from about 2 to about 200 mg component (a), e.g. Ciclosporin, per unit dosage.

Suitable dosage forms for oral administration include e.g. liquids, granulates and the like. Preferred however are solid unit dosage forms, for example tabletted or encapsulated forms, in particular hard or soft gelatin encapsulated forms. Such oral unit dosage forms will suitably comprise from about 5 to about 250 mg (e.g. about 5 to 200 or about 20 to 250 mg) cyclosporin per unit dosage. More suitably they will comprise from about 10, 20 or 25 to about 100 mg, e.g. 15, 20, 25, 50, 75 or 100 mg, component (a), e.g. Ciclosporin, per unit dosage.

Compositions in accordance with the present invention comprising a component (c) as aforesaid have the further advantage that they are capable of providing the basis for compositions exhibiting modified release characteristics, for example delayed release of component (a) or release of component (a) over prolonged periods of time, e.g. following oral administration. Such compositions additionally comprise (d), a component capable of modifying the release characteristics of the composition with respect to component (a). Such components (d) include, for example, polymeric excipients, in particular thickening agents, e.g. polymeric or colloidal thickening agents, as well as agents which are swellable in water, e.g. water-swellable polymers or colloids.

Suitable components (d) are known from the art and include:

$d^1$) Polyacrylate and polyacrylate co-polymer resins, for example poly-acrylic acid and poly-acrylic acid-methacrylic acid resins, such as known and commercially available under the trade name Carbopol (c.f. Fiedler, loc. cit., 1, p.p. 206–207), in particular the products Carbopol 934, 940 and 941, and Eudragit (c.f. Fiedler, loc. cit., 1, p.p. 372–373), in particular the products Eudragit E, L, S, RL and RS and, most especially, the products Eudragit E, L and S;

$d^2$) Celluloses and cellulose derivatives including: alkyl celluloses, e.g. methyl-, ethyl- and propyl-celluloses; hydroxyalkyl-celluloses, e.g. hydroxypropyl-celluloses and hydroxypropylalkyl-celluloses such as hydroxypropyl-methyl-celluloses; acylated celluloses, e.g. cellulose- acetates, cellulose-acetatephthallates, cellulose-acetatesuccinates and hydroxypropylmethyl-cellulose phthallates; and salts thereof such as sodium-carboxymethyl-celluloses. Examples of such products suitable for use in accordance with the present invention are those known and commercially available, e.g. under the trade names Klucel and Methocel (c.f. Fiedler, loc. cit., 1. p.p. 521 and 2, p.p. 601), in particular the products Klucel LF, MF, GF and HF and Methocel K 100, K 15M, K 100M, E 5M, E 15, E 15M and E 100M.

$d^3$) Polyvinylpyrrolidones, including for example poly-N-vinylpyrrolidones and vinylpyrrolidone co-polymers such as vinylpyrrolidone-vinylacetate co-polymers. Examples of such compounds suitable for use in accordance with the present invention are those known and commercially available, e.g. under the trade name Kollidon (c.f. Fiedler, loc. cit., 1, p.p. 526 and 527), in particular the products Kollidon 30 and 90.

$d^4$) Polyvinyl resins, e.g. including polyvinyl acetates and polyvinyl alcohols, as well as other polymeric materials including gum traganth, gum arabicum, alginates, e.g. alginic acid, and salts thereof, e.g. sodium alginates.

$d^5$) Silicon dioxides, including hydrophilic silicon dioxide products, e.g. alkylated (for example methylated) silica gels, in particular colloidal silicon dioxide products as known and commercially available under the trade name Aerosil [c.f. Handbook of Pharmaceutical Excipients, published by the Pharmaceutical Society of Great Britain, p.p. 253 to 256] in particular the products Aerosil 130, 200, 300, 380, 0, OX 50, TT 600, MOX 80, MOX 170, LK 84 and the methylated Aerosil R 972.

When a component (d) is present, it is suitably present in an amount of from about 0.5 to 50%, more preferably from about 1 to 20%, most preferably from about 2 to 10% by weight, based on the total weight of components (a)+(b)+(c)+(d).

When component (c) in the compositions of the invention comprises a solid carrier this is suitably: ($c^6$) a solid polymeric carrier as required by definition (vi) hereinbefore. Such polymeric carriers are preferably a water insoluble, or substantially water insoluble, polymeric carriers.

Especially preferred as components ($c^6$) are polyvinylpyrrolidones [c.f. Fiedler, loc. cit., 2, p.p. 748–750], including, especially, cross-linked polyvinylpyrrolidones. Examples of such materials suitable for use in the present invention are those known and commercially available under the trade name Kollidon [c.f. Fiedler, loc. cit., 1, p.p. 527], Kollisept [c.f. Fiedler, loc. cit., 2, p.p. 719–720], Povidone and Crospovidone [c.f. Fiedler, loc. cit., 2, p.p. 751].

Especially suitable components ($c^6$) are polyvinylpyrrolidones having a molecular weight of at least ca. 10,000 more suitably at least ca. 20,000 or 25,000, e.g. having a molecular weight of ca. 40,000 or more. Cross-linked polyvinylpyrrolidones are of particular interest. Examples of specific products suitable for use in the present invention as ($c^6$) are: Plasdone XL, Plasdone XL 10 and Crospovidone.

When the compositions of the invention comprise a component ($c^6$) they preferably also comprise (d), a water swellable or water soluble component, for example a cellulose or cellulose derivative as defined under ($d^2$) hereinabove.

Further examples of such materials of particular interest in relation to compositions of the invention comprising a component ($c^6$) are those known and commercially available under the trade names Avicel [c.f. Fiedler, loc. cit., 1, p.p. 160–161], Elcema [c.f. Fiedler, loc. cit., 1, p.p. 326] and Pharmacoat [c.f. Fiedler, loc. cit., 2, p.p. 707], for example the products Avicel PH 101 and PH 102, Elcema and Pharmacoat 603.

In the case of compositions of the invention comprising a component ($c^6$), component (a) is preferably present in component (b) in solid solution, including solid miscellar solution, e.g. entirely, or substantially entirely, in molecular or miscellar dispersion. [In practice components (b) will frequently exhibit at least a degree of fluidity, e.g. at ambient or slightly elevated temperature, and hence not be in the strictest sense "solid". The term "solid solution" as used in the present specification and claims is to be interpreted accordingly, e.g. as including viscous or highly viscous systems.] The solid solution comprised by (a) and (b) is suitably dispersed, for example in particulate, e.g. fine particulate form within, e.g. throughout, component ($c^6$). Components ($c^6$) will thus generally serve in compositions of the invention as a disintegratable matrix for [(a)+(b)]. Components (d) will generally serve as agents assisting disintegration, e.g. on contact with the contents of the gastro-intestinal tract.

Compositions of the invention comprising a component ($c^6$) will also suitably comprise (e), a binder and/or lubricant. Materials suitable for use as binding agent/lubricants are in particular fatty acid and alkyl sulfonate salts, e.g. metal salts, e.g. having 10 or more carbon atoms in the fatty acid/alkyl moiety, for example $C_{10-22}$ fatty acid and $C_{10-22}$alkyl sulfonate alkali metal or alkaline earth metal salts, e.g. sodium calcium or magnesium salts. Examples of such materials suitable for use in the present invention are: sodium lauryl sulfate and magnesium stearate [c.f. Fiedler, loc. cit., 2, p.p. 584].

When compositions of the invention comprise a component ($c^6$), components (a) and (b) are suitably present in a ratio of about 1:2 to 20 (e.g. about 1:3.33 to 20), preferably about 1:2.5 to 10 (e.g. about 1:5 to 10), most preferably about 1:3 to 8 (e.g. about 1:6.25 to 8.33) p.p.w. [(a):(b)].

Components ($c^6$) are suitably present in compositions of the invention in an amount of at least 10%, more preferably at least 15%, yet more preferably at least 20% by weight based on the total weight of the composition. Appropriately components ($c^6$) are present in compositions of the invention in an amount of from 10 to 60%, more preferably of from 15 to 50% by weight, e.g. from ca. 20 to 40%, e.g. ca. 25, 30 or 35% by weight, based on the total weight of the composition.

When a component (d) is present, components (d) and ($c^6$) are suitably present in a ratio of ca. 1:0.5 to 4, more preferably ca. 1:1 to 3, most preferably ca. 1:1.5 to 2.5, e.g. ca. 1:2 or ca. 1:2.5 p.p.w. [(d):($c^6$)].

When a component (e) is present, components (e) and ($c^6$) are suitably present in a ratio of ca. 1:5 to 25, more preferably ca. 1:5 to 20, most preferably ca. 1:7 to 15 p.p.w. [(e):($c^6$)].

When the compositions of the invention comprise all three components ($c^6$), (d) and (e) these are suitably together present in an amount of from ca. 25 to 75%, more preferably ca. 30 to 65%, most preferably ca. 40 to 65% based on the total weight of the composition. The ratio of components [(a)+(b)]:[(c)+(d)+(e)] is suitably of the order of 1:0.25 to 7.5, more preferably 1:0.5 to 5, most preferably 1:0.5 to 2, e.g. ca. 1:0.8, 1:1.2 or 1:1.3 p.p.w.

Compositions in accordance with the invention comprising a component ($c^6$) may be made up in any appropriate dosage form, e.g. for oral or topical application. Suitably such compositions in accordance with the invention will be made up in unit dosage form, whether for oral administration or otherwise.

The amount of component (a) present in such unit dosage forms will of course vary depending on e.g. the condition to be treated, the intended mode of administration and the effect desired. In general however they will suitably comprise from about 2 to about 200 mg component (a), e.g. Ciclosporin, per unit dosage.

Suitable dosage forms for oral administration include granulates and the like. Preferred however are solid unit dosage forms, for example tabletted or encapsulated forms. Such oral unit dosage forms will suitably comprise from about 5 to about 250 mg (e.g. about 5 to 200 or about 20 to 250 mg) cyclosporin per unit dosage. More suitably they will comprise from about 10, 20 or 25 to about 100 mg, e.g. 15, 20, 25, 50, 75 or 100 mg, component (a), e.g. Ciclosporin, per unit dosage.

Component (c) in the compositions of the invention may also comprise: ($c^7$) citric acid, an organosilicon oxide polymer or a mineral oil, e.g. a paraffin for example paraffinum per- or subliquidum [as required by definition (vi) hereinbefore]. For use in the compositions of the invention organosilicon oxide polymer or mineral oil components ($c^7$) are preferably readily flowable at temperatures of up to 150° C., preferably up to 100° C., more preferably up to 50° C. Suitably such components ($c^7$) have a maximum viscosity of 15,000 mPa.s., more preferably 1,000 mPa.s. at the indicated temperatures.

When ($c^7$) comprises citric acid, the composition may also suitably comprise a disintigrating agent, for example capable of gas generation on contact with water, e.g. sodium bicarbonate, to provide an effervescent product capable of ready dissolution in water or other drinkable liquid medium, prior to ingestion, as hereinafter described in example 8.

When ($c^7$) comprises citric acid, components (a) and (b) are suitably present in a ratio of about 1:5 to 7.5, e.g. about 1:6.25 p.p.w. [(a):(b)]. Components (a) and ($c^7$) are suitably present in a ratio of about 1:5 to 10, e.g. about 1:7.5 p.p.w. [(a):(b)]. When a disintegrating agent, e.g. sodium bicarbonate, is present this is suitably present in an amount of about 15 to 25%, e.g. about 17%, based on the total weight of the composition.

Mineral oils, e.g. paraffin hydrocarbons, suitable for use as component ($c^7$) preferably comprise liquid and semi-solid paraffins, i.e. paraffinum subliquidum and paraffinum perliquidum [see Fiedler loc.cit., 2, p.p. 690–691], and mixtures thereof. To permit ready formulation, component ($c^7$) will suitably consist or consist essentially of fluid, or semi-solid paraffins, i.e. paraffinum perliquidum or paraffinum subliquidum, or mixtures thereof. Where however it is desired to produce compositions having e.g. slower active ingredient release characteristics, this may be achieved by the further addition of a solid paraffin, i.e. paraffinum durum.

When component ($c^7$) comprises a mineral oil, components (a) and ($c^7$) are suitably present in the compositions of the invention in a ratio of from about 1:6 to 200 p.p.w. [(a):($c^7$)]. When compositions in accordance with the invention comprise liquid or semi-solid paraffins only as component ($c^7$) these are preferably present in a ratio of from ca. 1:0.5 to 1.0 [liquid: semi-solid]. In this case components (a) and ($c^7$) are suitably present in a ratio of from ca. 1:6 to 200, more preferably ca. 1:6 to 100, most preferably 1:6 to 20, e.g. ca. 1:8 p.p.w. [(a):(c)].

When compositions in accordance with the invention additionally comprise a solid paraffin as component ($c^7$), the ratio of liquid/semi-solid paraffin:solid paraffin components is suitably ca. 1:0.06 to 0.1 p.p.w. In this case components (a) and ($c^7$) are suitably present in a ratio of from 1:6 to 200, more preferably 1:6 to 100, most preferably 1:8 to 20, e.g. ca. 1:10 p.p.w. [(a):($c^7$)].

Organosilicon oxide polymers suitable for use as component ($c^7$) include, in particular, fluid, i.e. liquid and semi-solid polymeric materials having a structural unit of formula —(R)$_2$Si—O— in which each R is a monovalent organic radical, for example $C_{1-4}$ alkyl, especially methyl, or phenyl. Especially preferred are organosiloxane polymers having a viscosity of from ca. 0.65 to $10^5$ cP, especially of from ca. 10 or 50 to 500 or 1,000 cP.

To permit ready formulation, component ($c^7$) suitably comprises liquid organosiloxane polymers, e.g. polymethylsiloxane polymers, e.g. any of the various known silicon oils, such as silicon oil 550, DC 200, SF-1066 and SF-1091 [c.f. Fiedler, loc. cit.,2, p.p. 826]. When compositions in accordance with the invention comprise liquid organosiloxane polymers only, components (a) and ($c^7$) are suitably present in a ratio of from ca. 1:6 to 200, more preferably ca. 1:6 to 100, most preferably 1:6 to 20, e.g. ca. 1:8 p.p.w. [(a):($c^7$)].

Compositions having e.g. slower active ingredient release characteristics may be achieved use of semi-solid organosiloxane polymers, e.g. any of the various known silicon pastes, e.g. silicon paste A [c.f. Fiedler, loc. cit., 2, p.p. 826] as component ($c^7$) or by addition of these, e.g. to other organosilicon oxide polymers as described above. In the latter case, the ratio of liquid:semi-solid organosilicon polymers present in the composition of the invention is suitably of the order of from ca. 1:0.5 to 1. In this case the ratio of components (a):($c^7$) is suitably of the order of from ca. 1:6 to 100, preferably ca. 1:6 to 20 p.p.w. [(a):($c^7$)].

As will be appreciated, mixtures of components ($c^7$) as defined may also be employed in the compositions of the invention.

When compositions of the invention comprise a mineral oil or organosiloxane polymer as component ($c^7$), components (a) and (b) are suitably present in a ratio of about 1:3.33 to 20, preferably about 1:6 to 20 p.p.w. [(a):(b)]. More preferably they are present in a ratio of about 1:6 to 10 (e.g. about 1:6.25 to 8.33), most preferably about 1:6.0 to 6.5, e.g. about 1:6.25 p.p.w. [(a):(b)].

In the case of compositions of the invention comprising a component ($c^7$), component (a) is present in component (b)

entirely, or substantially entirely in molecular or miscellar dispersion, e.g. in the form of a solid solution or solid miscellar solution [whereby the term "solid solution" is employed here in the same broad sense as in relation to compositions a component ($c^6$)]. The solid solution comprised by (a) and (b) is suitably dispersed in particulate, e.g. fine particulate, form with component ($c^7$), e.g. throughout component ($c^7$).

Compositions in accordance with the invention comprising a component ($c^7$) may be made up in any appropriate dosage form, e.g. for oral, parenteral or topical application, for example for dermal or ophthalmic application, e.g. for application to the surface of the eye, e.g. for the treatment of autoimmune conditions of the eye such as hereinbefore set forth, or for intra-lesional injection, e.g. in the treatment of psoriasis. Suitably they will be made up in unit dosage form, whether for oral administration or otherwise.

The amount of component (a) present in such unit dosage forms will of course vary depending on e.g. the condition to be treated, the intended mode of administration and the effect desired. In general however, they will suitably comprise from about 2 to about 200 or 250 mg component (a), e.g. Ciclosporin, per unit dosage.

Suitable dosage forms for oral administration include liquids, granulates and the like. Preferred however are solid unit dosage forms, for example tabletted or encapsulated forms, in particular hard or soft gelatin encapsulated forms. Such oral unit dosage forms will suitably comprise from about 5 to about 250 mg (e.g. about 5 to 200 mg) cyclosporin per unit dosage. More suitably they will comprise from about 10, 20 or 25 to about 100 mg, e.g. 15, 20, 25, 50, 75 or 100 mg, component (a), e.g. Ciclosporin, per unit dosage.

Compositions in accordance with the invention comprising a component ($c^7$), in particular a mineral oil or organosiloxane oxide polymer, have the further advantage that they are capable of providing the basis for compositions exhibiting modified release characteristics, for example delayed release of component (a), or release of component (a) over prolonged periods of time, e.g. following oral administration. Such compositions may be obtained as hereinbefore described by the inclusion of solid or semi-solid components ($c^7$) in appropriate amounts. Alternatively they may be obtained by inclusion of an additional component (d): a component capable of modifying the release characteristics of the composition with respect to component (a). Such components (d) include, for example, polymeric excipients, in particular thickening agents, e.g. polymeric or colloidal thickening agents, as well as agents which are swellable in water, e.g. water-swellable polymers or colloids, for example any of the materials defined under ($d^1$) to ($d^5$) hereinabove.

When a component (d) is present, this is suitably present in an amount of from about 0.5 to 30%, more preferably from about 1 to 20%, most preferably from about 1 to 10% based on the total weight of components (a)+(b)+($c^7$)+(d).

Components ($d^5$) are in particular indicated for use in compositions in accordance with the invention comprising an organosilicon oxide polymer as component ($c^7$).

Compositions in accordance with the invention comprising a component ($c^6$) or ($c^7$) will be, or will preferably be, non-aqueous or substantially non-aqueous, e.g. as hereinabove described in relation to compositions comprising other components (c).

Compositions in accordance with the present invention may, irrespective of the selected component (c) [e.g. whether component (c) comprises any one of components ($c^1$) to ($c^7$) hereinbefore set forth or any mixture thereof] include any additional additives, e.g. as known and conventionally employed in the art, for example antioxidants [e.g. ascorbyl-palmitate, tocopherols, butyl-hydroxy-anisole (BHA) or butyl-hydroxy-toluene (BHT)], flavouring agents and so forth.

In particular the compositions of the invention will also suitably comprise one or more stabilizers or buffering agents, in particular to prevent hydrolysis of component (b) or degradation of component (a) during processing or on storage. Such stabilizers may include acid stabilizers such as citric acid, acetic acid, tartaric acid or fumaric acid as well as basic stabilizers such as potassium hydrogen phosphate, glycine, lysine, arginine or tris(hydroxymethyl) aminomethane.

Such stabilizers or buffer agents will appropriately be added in an amount sufficient to achieve or maintain a pH within the range of from about 3 to 8, more preferably about 5 to 7, e.g. between 6 and 7. Such stabilizors will generally be present in an amount of up to 5% by weight based on the total weight of the composition, or up to 10% by weight, for example where citric or acetic acids are employed. Compositions in accordance with the invention, in particular compositions wherein component (a) is Ciclosporin, having a pH within the above indicated ranges are preferred.

Compositions in accordance with the invention will also suitably comprise a polyoxyalkylene-free tenside, such as for example dioctylsuccinate, dioctyl-sulfo-succinate, di[2-ethylhexyl]-succinate, sodium lauryl sulfate or phospholipids, e.g. lecithins. When a tenside as aforesaid is present, this is suitably present in an amount of from 5 to 50, more preferably 10 to 50, for example 10 to 25% based on the weight of component (b).

In the case of compositions of the invention comprising component (a) in solid solution in component (b), e.g. when component (c) is a component ($c^6$) or ($c^7$) as hereinbefore set forth, any stabilizers, buffers and/or tensides as aforesaid are suitably incorporated into the solid solution phase. Such materials may also be included in component (c) etc.

Compositions in accordance with the invention, again irrespective of the selected component (c), will preferably be free or substantially free of ethanol, e.g. contain less than 5.0%, more preferably less than 2.5%, e.g. from 0 to 1.0% of ethanol based on the total weight of the composition.

In addition to the foregoing, the present invention also provides a process for the preparation of a pharmaceutical composition as hereinbefore defined, which process comprises intimately admixing or compounding components (a), (b) and (c) as hereinbefore defined, optionally together with a component (d) and/or other component, e.g. stabilizor, buffer or tenside as hereinbefore described, and, when required, putting the obtained composition up in unit dosage form, for example unit dosage form for oral administration, e.g. by tabletting, filling into gelatin capsules or other suitable means.

When component (c) is a solvent for components (a) and (b), or comprises a component ($c^1$), ($c^2$), ($c^3$), ($c^4$) or ($c^5$) as hereinbefore defined, components (a), (b) and (c) are suitably brought together in the above process by dissolution of components (a) and (b) together in component (c), e.g. with warming at temperatures of from up to 50° or 150° C., preferably not above 70° or 75° C. The mixture thus obtained may then be further compounded with components (d) etc., e.g. by intimate admixture in accordance with techniques known in the art. Filling, e.g. into hard or soft gelatin capsules, is suitably performed at elevated temperature, e.g. up to 50° C., to attain composition fluidity, e.g. in the warm.

In the case of compositions in accordance with the invention comprising component (a) in solid solution in component (b), e.g. compositions comprising a component ($c^6$) or ($c^7$) as hereinbefore set forth, said process will suitably first comprise preparation of a solid solution of (a) in (b) followed by intimate admixture or compounding of the obtained solid solution with the remaining components (c) and, optionally, (d) etc.

Solid solutions comprising components (a) in (b) may be prepared in accordance with techniques known in the art, e.g. by solidification of a melt comprising (a) in solution in (b), or removal of the solvent from a solution of components (a) and (b). For the purposes of the present invention the latter alternative will generally be preferred.

Suitable solvents for components (a) and (b) include lower alkanols, e.g. ethanol. Stabilizors, buffers and/or tensides are suitably incorporated at the solution stage.

The solid solution thus obtained is then suitably compounded, e.g. in fine particulate form, with component (c) and, optionally, components (d) and (e) etc., e.g. by distribution in component (c).

Although ethanol may be employed for the purpose of preparing the compositions of the invention, e.g. in the preparation of solid solutions as described above, this will preferably be removed, e.g. by evaporation, prior to completion of the final dosage form to give an ethanol free or substantially ethanol free product as hereinbefore set forth.

The following examples are illustrative of the present invention.

The product saccharose monolaurate L-1695 employed in the examples is commercially available from Mitsubishi-Kasei Food Corp., Tokyo 104, Japan: HLB-value=at least 12.3: lauryl ester residue purity=at least 95%: M.P.=ca. 35° C.: decomposition at ca. 235° C.: surface tension of 0.1% by weight aqueous solution=ca. 72.0 dyn/cm at 25° C.

A) Preparation of solid solutions and their use

EXAMPLE 1

1000 mg of saccharose monolaurate L-1695 and 160 mg of Ciclosporin are dissolved in 20 ml of ethanol and the solvent evaporated in a Rotavaporisator to yield the desired solid solution. The residue is pulverised in a mortar under dry conditions, since the monoester is hygroscopic.

EXAMPLE 2

1000 mg of the saccharose monolaurate L-1695 are mixed with 160 mg of Ciclosporin and the mixture heated to 150° C. while stirring. The obtained clear solution is cooled to room temperature to yield the desired solid solution and then processed further as described in Example 1.

EXAMPLE 3 a) 1000 mg of the saccharose monolaurate L-1695 and 30 mg of Proquazone (Biarison$^R$) are dissolved in 20 ml of 100% ethanol and the solvent evaporated completely in a Rotavaporisator to yield the desired solid solution. The residue is reduced to a fine powder in a mortar and is mixed with 10 mg of magnesium stearate as a lubricator.

b) A similar solid solution is obtained by substituting the Proquazone ingredient with 30 mg of Progesterone.

EXAMPLE 4

Solid solutions having the following compositions are obtainable analogously to Example 1.

| SOLID SOLUTION | CICLOSPORIN CONTENT | SACCHAROSE MONOESTER CONTENT* |
|---|---|---|
| A | 120 mg | 1000 mg Saccharose monocaproate |
| B | 130 mg | 1000 mg Saccharose monomyristate |
| C | 250 mg | 1500 mg Saccharose monooleate |

*Monoester content for all listed esters >80%.

The obtained solid solutions are completely soluble in water.

EXAMPLE 5

Solid solutions containing Ciclosporin in 1000 mg of raffinose monolaurate and in 1000 mg of raffinose monooleate respectively (monoester content >80%) are prepared using the evaporation method. In the raffinose monolaurate 135 mg of Ciclosporin and in raffinose monooleate 200 mg of Ciclosporin could be dissolved. The obtained solid solutions are completely soluble in water.

EXAMPLE 6

2000 mg of saccharose monolaurate L-1695 and 320 mg of Ciclosporin are dissolved in 50 ml of an aqueous solution containing 10% of weight of ethanol and the liquid micellar solution is filled in ampoules for injection and lyophilised under sterile conditions. The thus obtained solid solution in the ampoule can be dissolved within 30 seconds by shaking in a 0.9% NaCl containing aqueous solution to yield a clear solution as product.

EXAMPLE 7

1000 mg of saccharose monolaurate (monoester content >80%) and 30 mg of Proquazone (Biarison$^R$) are processed according to the evaporation method to a solid solution. The powder is moulded with 1.0 g of Adeps solidus Ph. Eur. to a suppository, thus diminishing the hygroscopicity.

B) Preparation of compositions comprising a component (a), (b) and (c) as hereinbefore set forth.

EXAMPLE 8

362 mg of a solid solution prepared according to the method of Example 1 are mixed with 375 mg of water free citric acid and 150 mg of sodium bicarbonate and the mixture pressed. The thus obtained effervescent tablet contains 50 mg of Ciclosporin and dissolves within 2.5 minutes in water without leaving a residue. The obtained solution is adminsterable orally to provide effective Ciclosporin therapy, e.g. on administration of one or several such dosages, e.g. 2 to 4× per day.

EXAMPLE 9

181.25 mg of a solid solution, prepared according to the method of Example 1 containing 25 mg of Ciclosporin are mixed while stirring with 198.75 mg of viscous liquid paraffin and filled into hard gelatine capsules. The release rate of Ciclosporin from the obtained oral unit dosage form is measured in water at 37° C.:

| Time (min.) | % of weight of Ciclosporin dissolved | standard deviation mean value (nn = 3) |
|---|---|---|
| 5 | 3 | 2,2 |
| 10 | 14 | 3,5 |
| 15 | 29 | 6,8 |
| 30 | 65 | 7,0 |
| 60 | 98 | 0,6 |
| 120 | 98 | 0,6 |
| 180 | 98 | 0,6 |

C) Preparation of a liquid micellar solution and its use

For human application the solid solution is preferably transformed into a liquid (aqueous) micellar solution, of which generally a dosis is used corresponding to an amount of 40 to 2000 mg of Ciclosporin for oral or intravenous application. For the oral application the higher dosage and for intravenous application the lower dosage within the range are taken.

EXAMPLE 10

16 mg of Ciclosporin are solubilised in 1 ml of an isotonic aqueous solution of 10% of weight of saccharose monolaurate L-1695. The solution is used for the treatment of Psoriasis by intralesional injection. Repeated injection is effective in the treatment of Psoriasis.

EXAMPLE 11

1000 mg of saccharose monolaurate L-1695 and 160 mg of Ciclosporin are dissolved in a liquid mixture of 16 ml of 1.2-propylene glycol and 91 ml of distilled water, sterilised by filtration and filled in an ampoule for injection. The dosage of 1.5 mg of Ciclosporin pro ml of solubilisate solution corresponds to the average dosage range and a dilution to a ratio of 1:33 of the normal Ciclosporin infusion concentrate of 50 mg/ml.

EXAMPLE 12

With p-hydroxy benzoic acid methyl ester as a substantially water insoluble excipient, Proquazone (Biarison$^R$) and Progesterone as substantially water insoluble pharmaceutically active compounds, clear solubilisate solutions are prepared with saccharose monolaurate L-1695. In an aqueous solution of solubilisate (10% by weight) 8 mg of p-hydroxybenzoic acid methyl ester, 3 mg of Proquazone and 3 mg of Progesterone can be solubilised per ml. The solubilisate solutions are stable over a long period of time at room temperature. A solid solution is obtained by removing the water by freeze drying.

D) Preparation of compositions comprising a component (a), (b) and (c) as hereinbefore set forth.

EXAMPLES

| | INGREDIENT | RELATIVE AMOUNT (mg) |
|---|---|---|
| 13. a) | Cyclosporin (e.g. Ciclosporin) | 50.0 |
| b) | Saccharose monolaurate L-1695 | 312.5 |
| c) | 1,2-propylene glycol | 100.0 |
| | TOTAL | 462.5 |
| 14. a) | Cyclosporin (e.g. Ciclosporin) | 50.0 |
| b) | Saccharose monolaurate L-1695 | 312.5 |
| c) | Glycerol | 100.0 |
| | TOTAL | 462.5 |

-continued

| | INGREDIENT | RELATIVE AMOUNT (mg) |
|---|---|---|
| 15. a) | Cyclosporin (e.g. Ciclosporin) | 50.0 |
| b) | Saccharose monolaurate L-1695 | 312.5 |
| c) | PEG 200 | 100.0 |
| | TOTAL | 462.5 |
| 16. a) | Cyclosporin (e.g. Ciclosporin) | 50.0 |
| b) | Saccharose monolaurate L-1695 | 312.5 |
| c) | PEG 400 | 100.0 |
| | TOTAL | 462.5 |
| 17. a) | Cyclosporin (e.g. Ciclosporin) | 50.0 |
| b) | Saccharose monolaurate L-1695 | 350.0 |
| c) | 1,2-propylene glycol | 100.0 |
| d) | Eudragit E | 50.0 |
| | TOTAL | 550.0 |
| 18. a) | Cyclosporin (e.g. Ciclosporin) | 50.0 |
| b) | Saccharose monolaurate L-1695 | 350.0 |
| c) | 1,2-propylene glycol | 100.0 |
| d) | Methocel K100 | 110.0 |
| | TOTAL | 610.0 |
| 19. a) | Cyclosporin (e.g. Ciclosporin) | 50.0 |
| b) | Saccharose monolaurate L-1695 | 350.0 |
| c) | 1,2-propylene glycol | 100.0 |
| d) | Aerosil 200 | 15.0 |
| | TOTAL | 515.0 |
| 20. a) | Cyclosporin (e.g. Ciclosporin) | 50.0 |
| b) | Saccharose monolaurate L-1695 | 350.0 |
| c) | PEG 400 | 200.0 |
| d) | Eudragit L | 2.5 |
| | TOTAL | 602.5 |
| 21. a) | Cyclosporin (e.g. Ciclosporin) | 50.0 |
| b) | Saccharose monolaurate L-1695 | 312.5 |
| c) | Gelucir (e.g. Gelucir 42/12, 44/14 or 35/10) | 100.0 |
| | TOTAL | 462.5 |
| 22. a) | Cyclosporin (e.g. Ciclosporin) | 50.0 |
| b) | Saccharose monolaurate L-1695 | 312.5 |
| c) | Gelucir | 100.0 |
| d) | Klucel LF | 50.0 |
| | TOTAL | 512.5 |

The composition of example 13 is prepared by dissolving components (a) and (b) with stirring and warming over an oil bath at 100° C. in component (c). The compositions of examples 14 to 22 are prepared analogously. In the case of examples 17 and 20 component (d) is dissolved in the initially obtained mixture of components (a) to (c). In the case of examples 18, 19 and 22 component (d) is suspended in (a) to (c).

The obtained compositions are filled, with warming, into hard gelatin capsules, size 1 (examples 13 to 15 and 21), or size 0 (examples 17 to 19 and 22), to give an encapsulated end-product with each capsule containing 50 mg cyclosporin (e.g. Ciclosporin) and suitable for administration for the prevention of transplant rejection or in the treatment of auto-immune diseases, e.g. on administration of from 1 to 5 capsules daily.

EXAMPLES

| | INGREDIENT | RELATIVE AMOUNT (mg) |
|---|---|---|
| 23. a) | Cyclosporin (e.g. Ciclosporin) | 100.0 |
| b) | Saccharose monolaurate L-1695 | 300.0 |

-continued

| | INGREDIENT | RELATIVE AMOUNT (mg) |
|---|---|---|
| c) | Plasdone XL | 350.0 |
| d) | Avicel PH 102 | 150.0 |
| e) | Sodium-laurylsulfate | 25.0 |
| | TOTAL | 925.0 |
| 24. a) | Cyclosporin (e.g. Ciclosporin) | 50.0 |
| b¹) | Saccharose monolaurate L-1695 | 350.0 |
| b²) | Saccharose monostearate | 50.0 |
| c) | Crospovidone | 250.0 |
| d) | Elcema | 150.0 |
| e) | Magnesium-stearate | 30.0 |
| | TOTAL | 980.0 |
| 25. a) | Cyclosporin (e.g. Ciclosporin) | 50.0 |
| b) | Saccharose monolaurate L-1695 | 160.0 |
| c) | Plasdone XL 10 | 200.0 |
| d¹) | Pharmacoate 603 | 25..0 |
| d²) | Avicel PH 101 | 75.0 |
| e) | Magnesium-stearate | 20.0 |
| | TOTAL | 605.0 |

The above compositions 23 to 25 each suitably additionally comprise 25 mg (f) tartaric acid and/or 50 mg (g) dioctyl succinate, preferably both, giving an end weight: for composition 23 of 1,000 mg; for composition 24 of 1,055 mg; and for composition 25 of 6180 mg.

Compositions 23 to 25 are prepared as follows: Components (a) and (b) are dissolved in absolute ethanol and the ethanol evaporated exhaustively at 50° C. under reduced pressure. Components (c) to (e) are thoroughly admixed [with addition of (f) and (g) when used] employing conventional mixing techniques. The solid solution comprising [(a)+(b)] is milled to a fine powder and mixed uniformly into [(c)–(g)] and the resultant uniform mass pressed into tablets each containing 100, 50 or 25 mg (a) and suitable for administration for the prevention of transplant rejection or in the treatment of auto-immune diseases, e.g. on administration of from 1 to 5 tablets daily.

EXAMPLES

| | INGREDIENT | RELATIVE AMOUNT (mg) |
|---|---|---|
| 26. a) | Cyclosporin (e.g. Ciclosporin) | 50.0 |
| b) | Saccharose monolaurate L-1695 | 312.5 |
| c) | Paraffinum perliquidum | 397.5 |
| | TOTAL | 760.0 |
| 27. a) | Cyclosporin (e.g. Ciclosporin) | 50.0 |
| b) | Saccharose monolaurate L-1695 | 312.5 |
| c) | Silicon oil DC 200 | 397.5 |
| | TOTAL | 760.0 |

Components (a) and (b) are dissolved in absolute ethanol and the ethanol evaporated exhaustively at 50° C. under reduced pressure. The obtained solid solution is milled to a fine powder and suspended uniformly in component (c). The obtained liquid suspension is filled into hard gelatin capsules, size 0 to give an encapsulated end-product with each capsule containing 50 mg cyclosporin (e.g. Ciclosporin) and suitable for administration for the prevention of transplant rejection or in the treatment of auto-immune diseases, e.g. on administration of from 1 to 5 capsules daily.

EXAMPLES

| | INGREDIENT | RELATIVE AMOUNT (mg) |
|---|---|---|
| 28. a) | Cyclosporin (e.g. Ciclosporin) | 50.0 |
| b) | Saccharose monolaurate L-1695 | 312.5 |
| c) | Paraffinum subliquidum | 372.5 |
| d) | Paraffinum durum | 25.0 |
| | TOTAL | 760.0 |
| 29. a) | Cyclosporin (e.g. Ciclosporin) | 50.0 |
| b) | Saccharose monolaurate L-1695 | 312.5 |
| c) | Paraffinum perliquidum | 397.5 |
| d) | Aerosil | 10.0 |
| | TOTAL | 770.0 |

Compositions 28 and 29 are prepared analogously to 26 and 27 above. In the case of composition 28 (c) and (d) are first combined by melting and intimately stirring together. The solid solution comprising [(a)+(b)] is then suspended in [(c)+(d)]. In the case of composition 29, (d) is suspended, together with [(a)+(b)] in (c).

Equivalent compositions to those of examples 1 to 29 above may be prepared by substituting any other cyclosporin, e.g. [Nva]²-Ciclosporin, for Ciclosporin as component (a), or substituting any other fatty acid saccharide monoester, e.g. as hereinbefore set forth, for example raffinose monolaurate, for saccharose monolaurate as component (b) in each case in the same or equivalent amount or relative proportion.

Utility of compositions in accordance with the invention may be shown in animal or clinical trials, for example performed as follows:

BIOAVAILABILITY STUDY FOR COMPOSITIONS IN ACCORDANCE WITH THE INVENTION IN THE DOG a) Test compositions

| COMPOSITION I | as per example | 13 |
|---|---|---|
| COMPOSITION II | as per example | 26 | b) Test method

Groups of 8 beagle dogs (male, ca. 11–13 kg) are used. Animals receive no food within 18 hours of administration of test composition but are allowed free access to water until administration. Test compositions are administered by gavage, followed by 20 ml NaCl 0.9% solution. The animals are allowed free access to food and water three hours after administration of test composition.

2 ml blood samples (or 5 ml for the blank) are taken from the vena saphena and collected in 5 ml plastic tubes containing EDTA at −15 min. (blank), 30 min., and 1, 1.5, 2, 3, 4, 6, 8, 12 and 24 hours post administration. Blood samples are stored at −18° C. pending assay.

Blood samples are analysed by RIA. Areas under the blood drug concentration versus time curves are calculated by the trapezoidal rule. Analysis of variance is performed with respect to AUC (area under curve), Cmax (maximum concentation) and Tmax (time of maximum).

c) Results

Calculated average AUC (in ng hr./ml$^{-1}$) and Cmax (in ng/ml$^{-1}$) values from typical trial runs are shown in the following table, together with calculated variation in response between test animals receiving the same composition (CV).

| COMPOSITION | AUC (0–24 h) | CV (%) | Cmax | CV % |
|---|---|---|---|---|
| I | 3058 | 19.9 | 583 | 30.9 |
| II | 2894 | 14.91 | 544 | 19.7 |

As will be seen from the above table, compositions in accordance with the invention exhibit high bioavailability (AUC and Cmax.) coupled with relatively low variability in subject response both for AUC and Cmax.

Comparable advantageous results may be obtained employing other compositions in accordance with examples 13 to 29 herein, in particular the compositions of example 13 to 22.

CLINICAL TRIAL

The advantageous properties of the compositions of the invention on oral administration may also be demonstrated in clinical trials, e.g. performed as follows:

Trial subjects are adult volunteers, e.g. professionally educated males of from 30 to 55 years. Trial groups suitably comprise 12 subjects.

The following inclusion/exclusion criteria are applied:

Inclusion: Normal screening ECG; normal blood-pressure and heart rate; body weight=50–95 kg.

Exclusion: Clinically significant intercurrent medical condition which might interfere with drug absorption, distribution, metabolism, excretion or safety; symptoms of a significant clinical illness in the two-week pre-trial period; clinically relevant abnormal laboratory values or electrocardiogram; need for concomitant medication during the entire course of the study; administration of any drug known to have a well-defined potential toxicity to a major organ system within the previous 3 months; administration of any investigational drug within 6 weeks prior to entry into the trial; history of drug or alcohol abuse; loss of 500 ml or more blood within the past 3 month period; adverse drug reaction or hypersensitivity; history of allergy requiring drug therapy; Hep.-B/HIV-positive.

Complete physical examination and ECG is performed pre- and post-trial. The following parameters are evaluated within 1-month periods pre- and post-trial:

Blood:—red blood cell count, haemoglobin, hematocrit, erythrocyte sedimentation, white blood cell count, smear, platelet count and fasting glucose;

Serum/plasma—total protein and electrophoresis, cholesterol, triglycerides, $Na^+$, $K^+$, $Fe^{++}$, $Ca^{++}$, $Cl^-$ creatinine, urea, uric acid, SGOT, SGPT, —GT, alkaline phosphatase, total bilirubin, α-amylase; Urine—pH, microalbumin, glucose, erythrocytes, ketone bodies, sediment.

Creatinine clearance is also determined 1-month prior to trial entry.

Subjects each receive trial compositions in randomised sequence. Compositions are administered orally, once to a total dose of 150 mg cyclosporin, e.g. Ciclosporin, and at least 14 days are allowed between each administration.

Administration is performed in the morning after an overnight fast of 10 hrs. with only water allowed. Only caffein-free beverages are permitted within the 24 hr. period following administration. Subjects are not allowed to smoke within the 12 hr. period following administration. Subjects receive a standardised lunch 4 hrs. following administration.

Blood samples (2 ml) are taken 1 hr. prior to administration and post-administration at 0.25, 0.5, 1, 1.5, 2, 2.5, 3, 3.5, 4, 4.5, 5, 6, 9, 12, 14, 24, 28 and 32 hrs. For determination of creatinine 2 ml blood samples are taken immediately prior to administration and at 12, 24 and 48 hrs. post-administration. Samples for cyclosporin determination are collected in two EDTA coated polystyrene tubes (1 ml each) at each time point and are deep frozen at -20° C. after gentle agitation. Cyclosporin is assayed in whole blood using RIA with specific and/or non-specific MAB assay—detection limit in both cases=ca. 10 ng/ml.

In trials carried out in accordance with the above protocoll, e.g. comparing the composition of example 13 in hard gelatin encapsulated form with the current Ciclosporin drink solution (Ciclosporin=50 mg, Labrafil=150 mg, ethanol=50 mg, maize oil=213 mg, in soft gelatin encapsulated form : content end weight=463 mg/dosage) as standard, substantially increased bioavailability levels for the example 13 composition are recorded in comparison with the standard as reflected in both AUC (0–32 hrs) and Cmax values established. In addition, comparison of variation in whole blood Ciclosporin concentration (as determined by specific monoclonal RIA) with time following single administration of test compositions to a Ciclosporin dosage of 150 mg, demonstrates marked reduction in variability of response between all subjects receiving composition in accordance with example 13 as compared with that for all subjects receiving the standard composition.

Similar or equivalent results may be obtained following oral administration of other compositions in accordance with the invention, e.g. as herein described in the examples, in particular examples 13 to 29.

We claim:

1. A water miscible composition comprising 7–30% cyclosporin in a solid solution of sucrose monolaurate or raffinose monolaurate.

2. The composition of claim 1 in which cyclosporin is in a solid solution of sucrose monolaurate.

* * * * *

UNITED STATES PATENT AND TRADEMARK OFFICE
CERTIFICATE OF CORRECTION

PATENT NO. : 5,756,450
DATED : May 26, 1998
INVENTOR(S) : Hahn, et al.

It is certified that error appears in the above-identified patent and that said Letters Patent is hereby corrected as shown below:

Title page: Item [73] should read:

-- Assignee: Novartis AG (formerly Sandoz Ltd.)
             Basel, Switzerland -- .

Signed and Sealed this

Twenty-third Day of May, 2000

Attest:

Q. TODD DICKINSON

*Attesting Officer*     *Director of Patents and Trademarks*